(12) United States Patent
Davey et al.

(10) Patent No.: US 12,734,332 B2
(45) Date of Patent: Sep. 15, 2026

(54) TELESCOPING CATHETER SYSTEM HAVING CLUTCH MECHANISM

(71) Applicant: Marvao Medical Devices, Ltd., Galway (IE)

(72) Inventors: Chris Davey, Barna (IE); John Culloty, Cork (IE); Sean Hehir, Dangan (IE)

(73) Assignee: Marvao Medical Devices, Ltd., Galway (IE)

( * ) Notice: Subject to any disclaimer, the term of this patent is extended or adjusted under 35 U.S.C. 154(b) by 0 days.

(21) Appl. No.: 19/106,446

(22) PCT Filed: Apr. 19, 2024

(86) PCT No.: PCT/IB2024/053861
§ 371 (c)(1),
(2) Date: Feb. 25, 2025

(87) PCT Pub. No.: WO2024/218748
PCT Pub. Date: Oct. 24, 2024

(65) Prior Publication Data
US 2026/0000866 A1 Jan. 1, 2026

Related U.S. Application Data

(60) Provisional application No. 63/622,806, filed on Jan. 19, 2024, provisional application No. 63/497,316, filed on Apr. 20, 2023.

(51) Int. Cl.
*A61M 25/01* (2006.01)
*A61M 25/00* (2006.01)

(52) U.S. Cl.
CPC ........ *A61M 25/01* (2013.01); *A61M 25/0097* (2013.01); *A61M 2025/0006* (2013.01); *A61M 2025/0175* (2013.01)

(58) Field of Classification Search
CPC .............. A61M 25/01; A61M 25/0097; A61M 2025/0006; A61M 2025/0175; A61M 25/00; A61M 2025/0004
See application file for complete search history.

(56) References Cited

U.S. PATENT DOCUMENTS 4,013,310 A * 3/1977 Dye ........................ F16L 37/05
285/423
5,120,323 A * 6/1992 Shockey ............... A61M 25/01
604/528

(Continued)

FOREIGN PATENT DOCUMENTS

WO WO 2015/113338 8/2015
WO WO 2023/052149 4/2023

OTHER PUBLICATIONS

International Search Report and Written Opinion were mailed on Jul. 16, 2024 by the International Searching Authority for International Application No. PCT/IB2024/053861 filed on Apr. 19, 2024 and published as WO2024218748 (Applicant—Chris Davey) (14 pages).

*Primary Examiner* — Rene T Towa
(74) *Attorney, Agent, or Firm* — Ballard Spahr LLP

(57) ABSTRACT

A telescoping catheter system equipped with a clutch mechanism that enables an Interventionalist to selectively lock inner and outer catheters together after adjusting their relative positions for optimal performance at the beginning of an interventional procedure, and to also unlock and reposition the catheters as needed to reestablish optimal performance at any subsequent point in the procedure.

14 Claims, 20 Drawing Sheets

(56) References Cited

U.S. PATENT DOCUMENTS

| | | | | |
|---|---|---|---|---|
| 5,397,310 | A * | 3/1995 | Chu | A61M 39/0613 604/167.03 |
| 2009/0312786 | A1* | 12/2009 | Trask | A61M 25/0606 606/191 |
| 2018/0200489 | A1* | 7/2018 | Gianotti | A61M 25/0136 |
| 2022/0323719 | A1* | 10/2022 | Rassat | A61M 25/0097 |

* cited by examiner

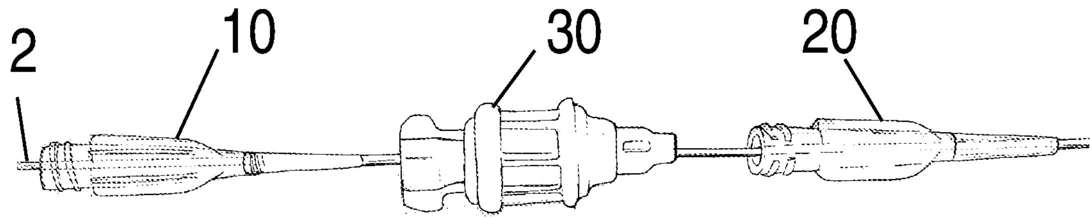
FIG. 8B
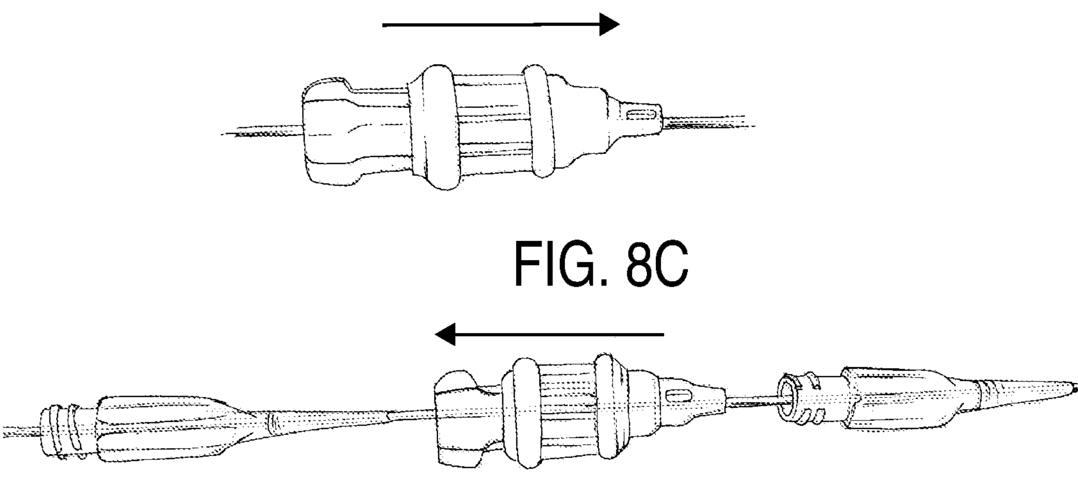
FIG. 8C
FIG. 8D

TELESCOPING CATHETER SYSTEM HAVING CLUTCH MECHANISM

CROSS-REFERENCE TO RELATED APPLICATIONS

This application is a national phase filing under 35 U.S.C. § 371 of International Application No. PCT/IB2024/053861, filed Apr. 19, 2024, which claims priority to and the benefit of the filing date of U.S. Provisional Patent Application No. 63/497,316, filed Apr. 20, 2023, and U.S. Provisional Patent Application No. 63/622,806, filed Jan. 19, 2024, the entire contents of which are hereby incorporated herein by reference.

BACKGROUND

Cardiovascular disease is a leading cause of death. The disease typically manifests by the formation of lesions within the arterial wall and lumen (FIG. 1) which, over time, increase in size and creates a localised restriction to blood flowing through the vasculature, resulting in damage to the downstream tissues and organs. Heart attacks are the leading cause of mortality in patients suffering from cardiovascular disease, which is cause by the sudden total blockage of blood flow in a coronary artery.

Another very significant cause of morbidity for patients suffering from cardiovascular disease is leg amputation, which is caused by the gradual blockage of blood flowing through the arteries in the legs down to the feet and toes which, over time, reduces the patient's ability to walk without pain and, if untreated, eventually cause the tissues in the foot to become ulcerated and/or gangrenous.

Patients who have been diagnosed with cardiovascular disease have multiple therapeutic options that range between lifestyle changes (diet, exercise, smoking cessation) and surgical revascularisation (bypass). Within this range are minimally invasive endovascular interventional techniques (balloon angioplasty, stenting, atherectomy, laser ablation etc) in which interventional catheters of various types are introduced into the vascular system, advanced to the location of the disease, and then used to open up the artery and restore healthy blood flow. Most, if not all, of these interventional techniques require the Interventionalist to first establish vascular access (FIG. 2) and then advance a guidewire through the patient's vascular system until the tip of the wire reaches the blockage, and then further advance the wire through/across the blockage so that it is then in position to act as a track over which the minimally invasive interventional catheter (balloon, atherectomy, ablation, and the like) can be advanced into position within the lesion. Proper placement of the guidewire across the lesion is an essential early step in the overall interventional process: if the guidewire cannot be placed across the lesion, the lesion cannot be treated by the interventionalist using any of these minimally invasive techniques. Those skilled in the art also appreciate that the greater the distance between the lesion and the vascular access site (FIG. 2) the more difficult it is for the Interventionalist to first reach the lesion, and subsequently position the guidewire across the lesion. Lesions in the smaller tibial arteries of the lower leg and the pedal arteries below the ankle require a greater degree of skill (and time) to reach and cross than the larger and more proximal lesions in femoral and iliac arteries above the knee. Guidewires by themselves are not stiff enough to both reach and cross these distal tibial and pedal lesions because they are necessarily designed to be flexible enough to be safely advanced through tortuous vascular pathways without causing damage to vessel walls and surrounding soft tissues. Interventionalists have had to develop compensating techniques whereby the flexible wire is advanced within a support catheter that accompanies the wire as it progresses deeper into the vasculature, providing added proximal stiffness and enabling the distal tip of the wire to be further advanced independently beyond the support catheter. Two support catheters arrange co-axially are often used in a telescoping fashion to provide enough support for a wire that needs to reach and cross multiple lesions, including total occlusions (FIG. 3) within the smaller tibial and pedal arteries of the lower leg and foot. The ability to simultaneously manipulate two support catheters and a guidewire under fluoroscopic guidance to reach and cross complex distal lesions presents a significant technical challenge that only the most skilled, experienced, and determined Interventionalists are capable of meeting. Therefore, a need exists for an improved co-axial telescoping support catheter system that simplifies and shortens the time required to reach and cross these types of lesions, thus improving the delivery of patient care and reducing healthcare costs.

SUMMARY

Disclosed herein, in various aspects, is a telescoping catheter system. The telescoping catheter system can have an inner catheter having a lumen configured to receive a guidewire, an outer catheter having a lumen configured to receive the inner catheter, and a clutch apparatus configured to selectively couple and decouple the inner and outer catheters. wherein when the clutch apparatus couples the inner and outer catheters together, the inner and outer catheters are configured for axial movement as a unitary structure, and wherein when the inner and outer catheters are decoupled, the inner and outer catheters are configured for independent telescoping axial movement.

In some aspects, when the clutch apparatus couples the inner and outer catheters together for axial movement as a unitary structure, the inner and outer catheters are configured to freely rotate relative to one another.

In some aspects, the inner catheter and the outer catheter have respective lengths, and the clutch apparatus is configured to couple the inner and outer catheters together via (a) compressive contact at multiple locations (e.g., any selected position) along the length of the inner catheter and (b) connection of the clutch apparatus to the hub of the outer catheter.

In some aspects, the outer catheter has a proximal hub, through which a portion of the inner catheter protrudes proximally from the outer catheter. In these aspects, the clutch apparatus can be incorporated into the hub of the outer catheter and used to selectively engage or disengage with at least one portion of the inner catheter that protrudes proximally from the outer catheter.

In some aspects, the clutch apparatus has a unitary body having opposing front and rear end portions and defining a lumen extending between the front and rear end portions. In these aspects, each of the front and rear end portions of the unitary body can be radially compressible. The front end portion of the unitary body can be configured for receipt within a hub of the outer catheter, and upon receipt of the front end portion of the unitary body within the hub of the outer catheter, inner surfaces of the hub of the outer catheter can be configured to effect radial compression of the front end portion of the unitary body to grip the inner catheter. The rear end portion of the unitary body can be selectively radially compressible by a radially inward force to permit manual gripping of the inner catheter.

In other aspects, the clutch apparatus has a body having opposing front and rear end portions and defining a lumen extending between the front and rear end portions. In these aspects, the rear end portion of the body is radially compressible, and the front end portion of the unitary body is configured for receipt within a hub of the outer catheter. The clutch apparatus can also include a locking collar that surrounds a portion of the body and is selectively slidable between: a first, forward position along a length of the body of the clutch apparatus in which the locking collar is axially spaced from the rear end portion of the body; and a second, rearward position along the length of the body in which the locking collar surrounds at least a portion of the rear end portion of the body to effect radial compression of the rear end portion of the body.

In some aspects, the hub of the outer catheter can include external threads, and the telescoping catheter system can further include a connector collar that surrounds at least a portion of the front end portion of the body and has internal threads that engage the external threads of the hub of the outer catheter when the clutch apparatus is used to couple the inner and outer catheters.

A method can include using clutch apparatus as disclosed herein to couple the inner and outer catheters together. With the inner and outer catheters coupled together, the method can further include selectively advancing a guidewire through the inner catheter.

Optionally, the method can further include using the clutch apparatus to decouple the inner and outer catheters.

Optionally, the method can further include axially translating the inner catheter relative to the outer catheter.

Also disclosed herein is a clutch apparatus for selectively coupling and decoupling inner and outer catheters, wherein a portion of the inner catheter protrudes proximally from the outer catheter. The clutch apparatus can include a body configured to be secured to a hub of the outer catheter and a collar slidably coupled to and positioned over the body. The collar can be configured for axial movement relative to the body in order to selectively engage or disengage the portion of the inner catheter that protrudes proximally from the outer catheter. The clutch apparatus can be configured to couple the inner and outer catheters together such that the inner and outer catheters are capable of axial movement as a unitary structure.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

FIG. 5A shows the clutch apparatus positioned roughly equidistant between the catheter hubs. FIG. 5B shows the clutch apparatus attached to an outer catheter hub. FIG. 5C is a close-up view of the engagement between the clutch apparatus and the outer catheter hub. FIG. 5D shows the clutch apparatus attached to the outer catheter hub and the inner catheter positioned such that the tips of both catheters are in close proximity to one another to maximise tip stiffness.

FIG. 6A is an external perspective view of the clutch apparatus having the sliding collar. FIG. 6B is an internal section view of the clutch apparatus of FIG. 6A. FIGS. 6C and 6D are internal section views of the clutch apparatus of FIG. 6A, respectively showing the sliding collar in a forward (disengaged) position (FIG. 6C) and a rearward (engaged) position (FIG. 6D) in which the clutch and the inner catheter shaft are axially locked to one another.

FIG. 7A is an external perspective view of the clutch apparatus, which the sliding collar in an open, disengaged position. FIG. 7B is an end view of the clutch apparatus of FIG. 7A. FIG. 7C is an internal section view of the clutch apparatus of FIG. 7A, depicting an exemplary insert (shown in this example as a soft compressible tube) that is deformed to exert compressive friction upon the internal catheter shaft.

FIGS. 8A-8E depict use of a clutch apparatus as shown in FIGS. 7A-7C. FIG. 8A depicts the clutch apparatus positioned roughly equidistant between the inner and outer catheter hubs, with the clutch apparatus free to slide along the inner catheter. FIG. 8B depicts the clutch apparatus with the slidable collar moved rearwardly to a locked position in which the slidable collar depresses compressible insert inwardly so that the clutch apparatus is locked in place on the inner catheter even without manual depression of the ramps. FIG. 8C is a close-up view of the clutch apparatus schematically depicting the unlocking of the clutch apparatus by sliding the slidable collar to a forward position. FIG. 8D is a schematic depiction of the locking of the clutch apparatus by sliding the slidable collar to a rear position. FIG. 8E depicts the clutch apparatus attached to the outer catheter hub and the inner catheter positioned such that the tips of both catheters are in close proximity to one another to maximize tip stiffness, with the inner catheter shaft being selectively locked or unlocked.

FIG. 9A is an external perspective view of the clutch apparatus in the open, forward position. FIG. 9B is an internal section view of the clutch apparatus of FIG. 9A, with the clutch apparatus in the closed, rear position, with one or more inner surfaces of the collar contacting the body of the clutch apparatus to compress the compressible insert into a friction fit with the internal catheter shaft. FIG. 9C is an internal section view of a clutch apparatus that is permanently secured to the outer catheter hub using adhesive applied through a glue hole, with the clutch apparatus disengaged from the inner catheter shaft such that the clutch apparatus (and outer catheter hub) are slidable along the length of the internal catheter shaft.

DETAILED DESCRIPTION

Figure 1:
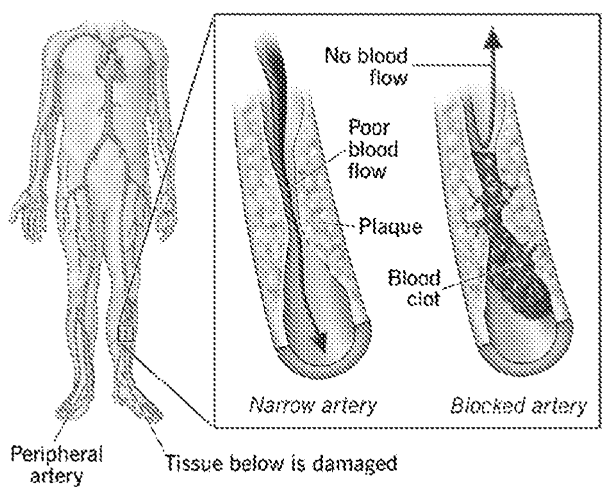
FIG. 1 is a schematic of the Peripheral Arterial System, including an illustration an exemplary atherosclerotic lesion as is typically found in patients with Peripheral Artery Disease.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" can include plural referents unless the context clearly dictates otherwise. For example, unless the context dictates otherwise, use of the term "a projection" can represent disclosure of "at least one projection" and is understood to provide support for embodiments in which a single one of such projections is provided and for embodiment in which a plurality of such projections are provided.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedents "about," "substantially," or "generally," it is contemplated that values within up to 15%, up to 10%, up to 5%, or up to 1% (above or below) of the particularly stated value can be included within the scope of those aspects. In other aspects, when angular values are approximated by use of the antecedents "about," "substantially," or "generally," it is contemplated that angular values within up to 15 degrees, up to 10 degrees, up to 5 degrees, or up to one degree (above or below) of the particularly stated angular value can be included within the scope of those aspects.

In the following description and claims, wherever the word "comprise" or "include" is used, it is understood that the words "comprise" and "include" can optionally be replaced with the words "consists essentially of" or "consists of" to form another embodiment.

As used herein, the words "proximal" and "rear" and variations thereof are intended to refer to a position, location, or direction that is toward or closer to the Interventionalist who is performing a procedure using a catheter system as disclosed herein, whereas the words "distal" and "front" and "forward" and variations thereof are intended to refer to a position, location, or direction that is moving away from or farther away from the Interventionalist. Thus, in general, it is understood that the inner catheter hub will be proximal to, or to the rear of, the outer catheter hub, whereas the clutch apparatus will be distal of the inner catheter hub and proximal of the outer catheter hub.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Introduction

Interventional procedures to restore flow in restricted or occluded blood vessels continue to evolve as new interventional devices are developed and adopted. Those skilled in the art know that clinical practice patterns vary significantly from one Interventionalist to another, but that these procedures include using entry and access devices to introduce a guidewire into the vascular system, then using diagnostic devices to map and image the blood vessels to be treated, followed by advancing a guidewire deeper into the vasculature until the guidewire is in position across the lesion to be treated, and then, finally, using the guidewire to support subsequent advancement of interventional devices into the lesion for use to open up the restriction and restore adequate blood flow to downstream tissues. Thus, the success of the Interventional procedure is dependent on the ability of the Interventionalist to advance a guidewire to the lesion, and to subsequently further advance the tip of the guidewire into and past the lesion.

Figure 2:
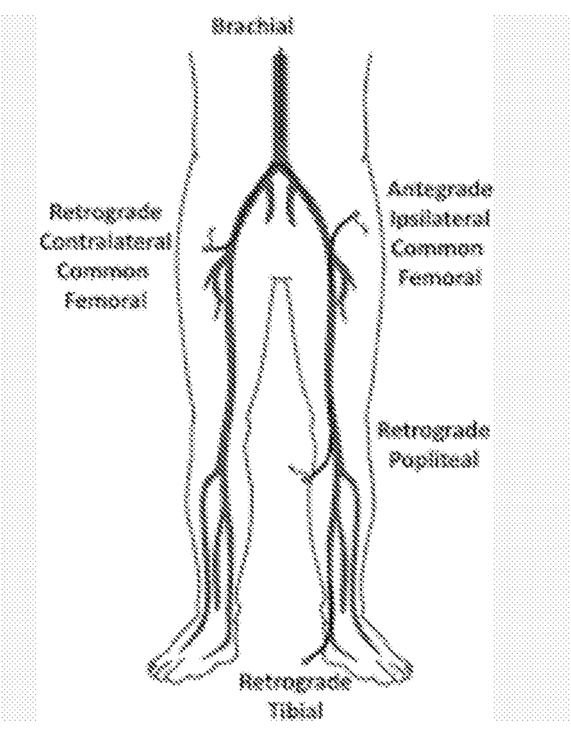
FIG. 2 is a schematic of the various vascular access points into the Peripheral Arterial System that an Interventionalist can use to initiate interventional treatment of Peripheral Artery lesions.

Vascular access is generally made in the relatively large superficial vessels of the leg, arm, or neck. A typical interventional procedure involves establishing vascular access into the common femoral artery, from which the Interventionalist can advance devices down to the peripheral arteries of the leg and foot, or up to the arteries of the torso, arms, neck and head. FIG. 1 shows a typical occulive lesion located in the tibial artery, and FIG. 2 shows the vascular access sites the Interventionalist could use to in order to treat that tibial lesion. The more distance and tortuosity between the access site and the lesion, the more frictional resistance that the devices must overcome during the procedure; thus the interventional devices must be designed with enough proximal stiffness to be pushed deeply into the vasculature but also enough distal flexibility to navigate and track through tortuous vascular pathways without causing injury to the vessels.

Figure 3:
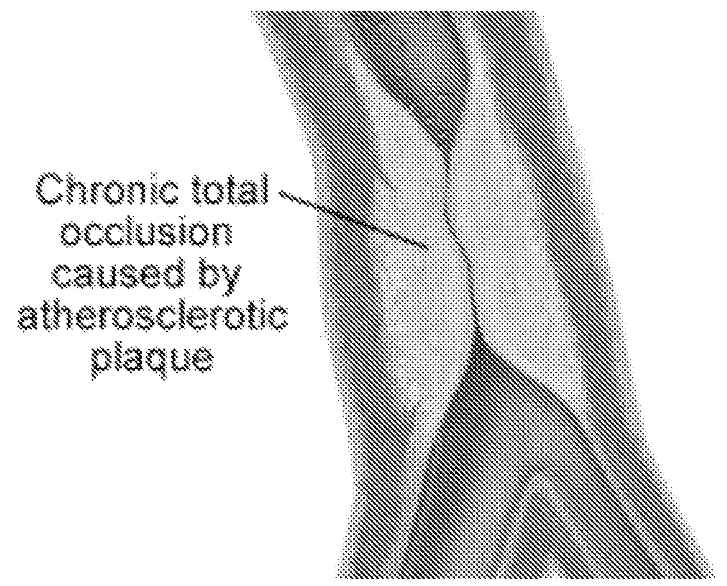
FIG. 3 is an illustration of a severe atherosclerotic lesion in which the artery is completely occluded, preventing the flow of blood to downstream tissues.
Figure 4A:
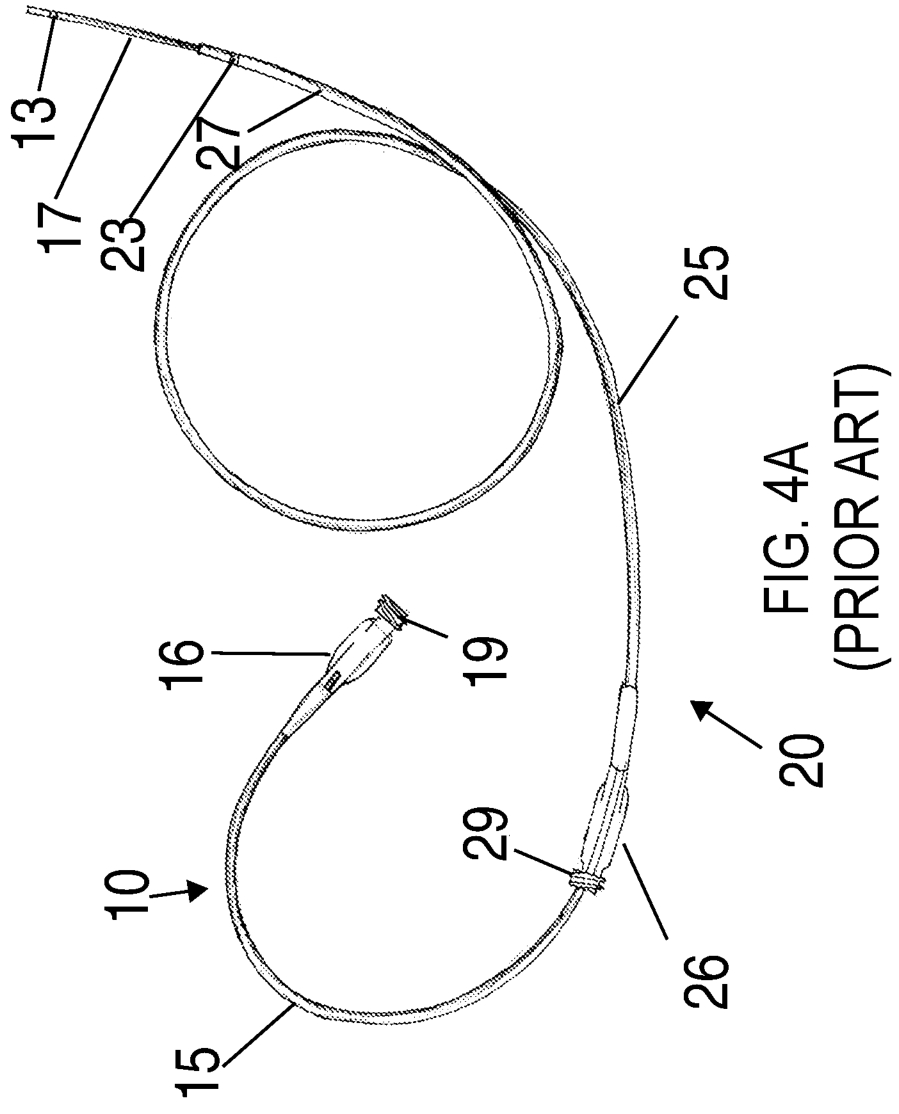
FIG. 4A depicts a conventional Telescoping Catheter System as configured during a typical Interventional procedure.
Figure 4B:
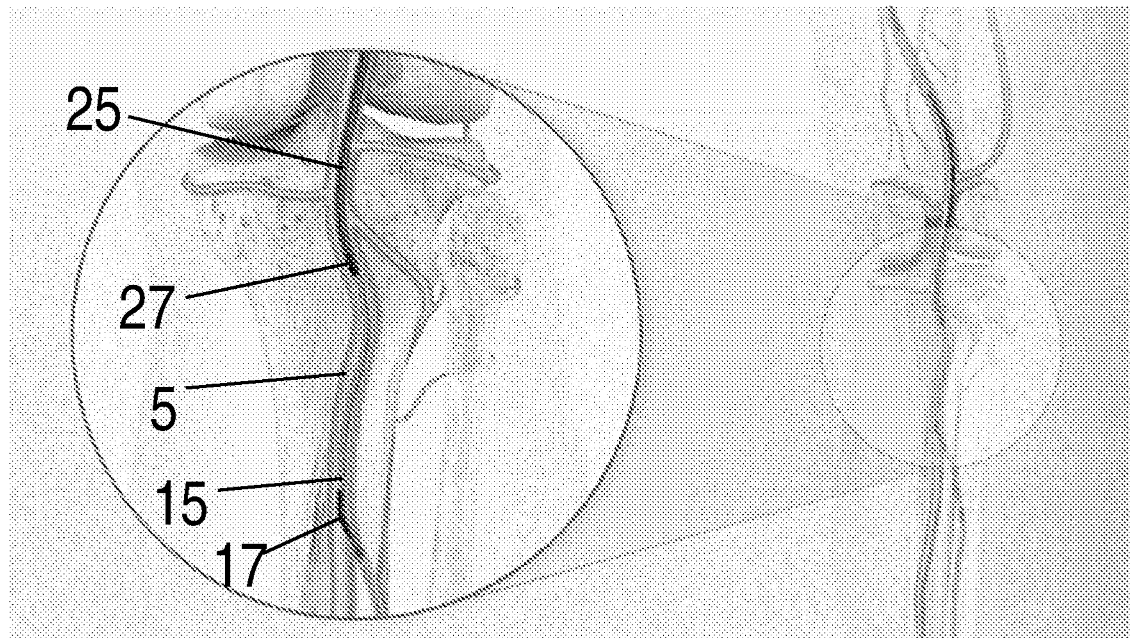
FIG. 4B depicts conventional telescoping catheter system tips in situ within a peripheral artery located behind the knee.
Figure 5A:
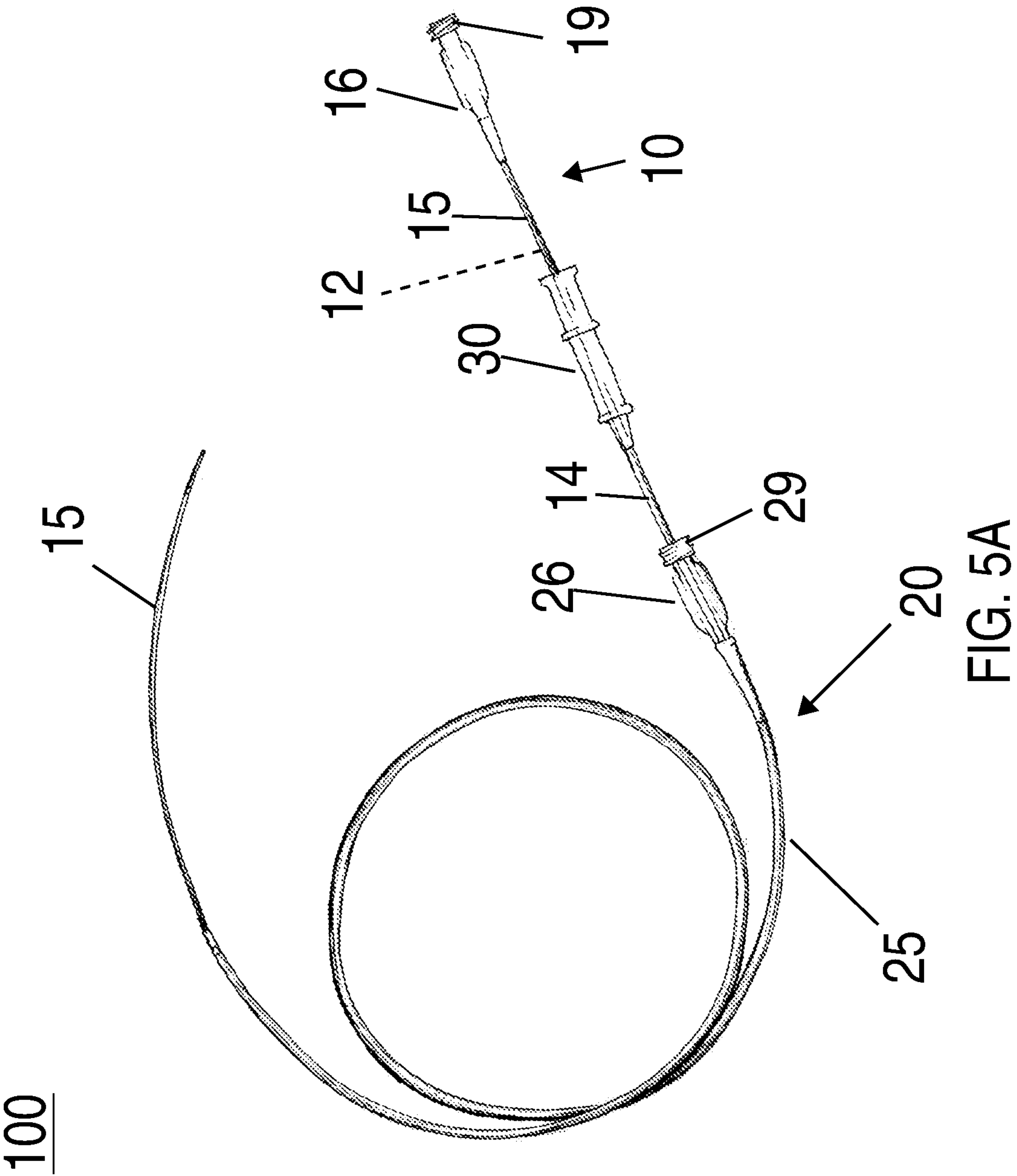
FIGS. 5A-5D depict an exemplary Telescoping Catheter System that has a clutch apparatus as disclosed herein.
Figure 5B:
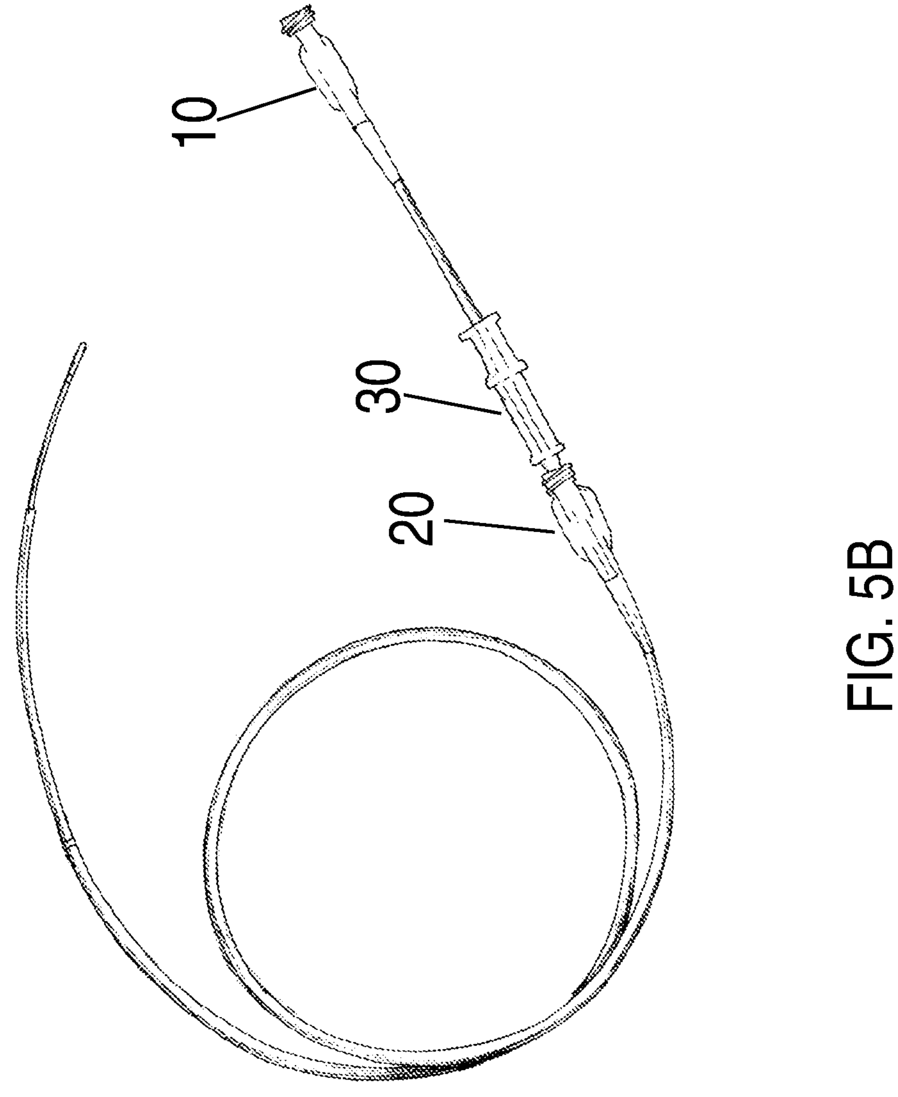
Figure 5C:
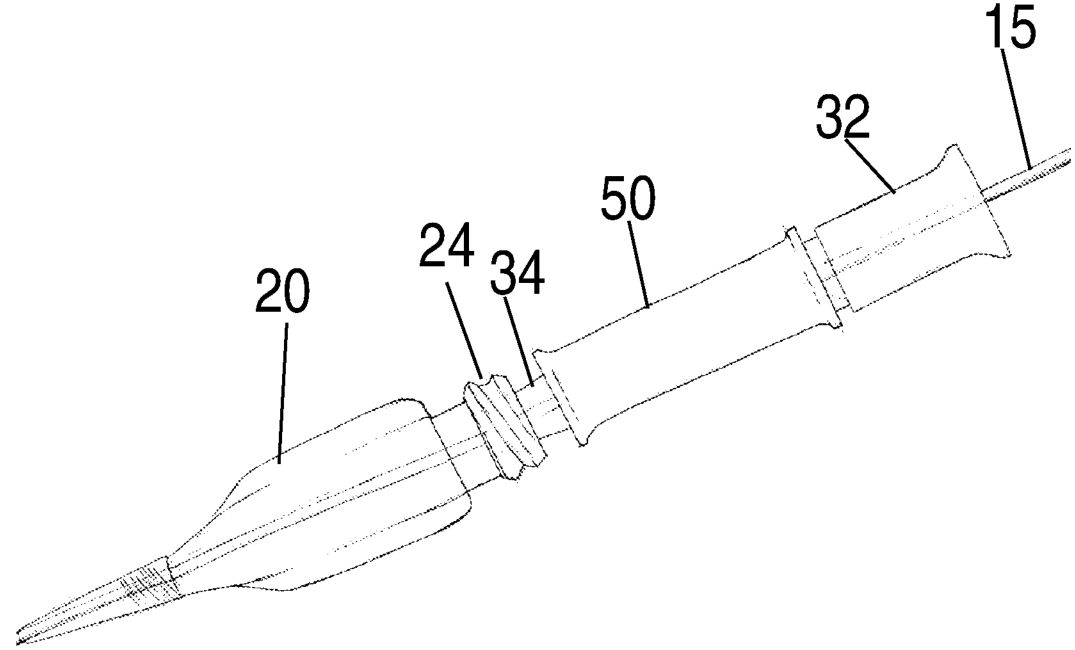
Figure 5D:
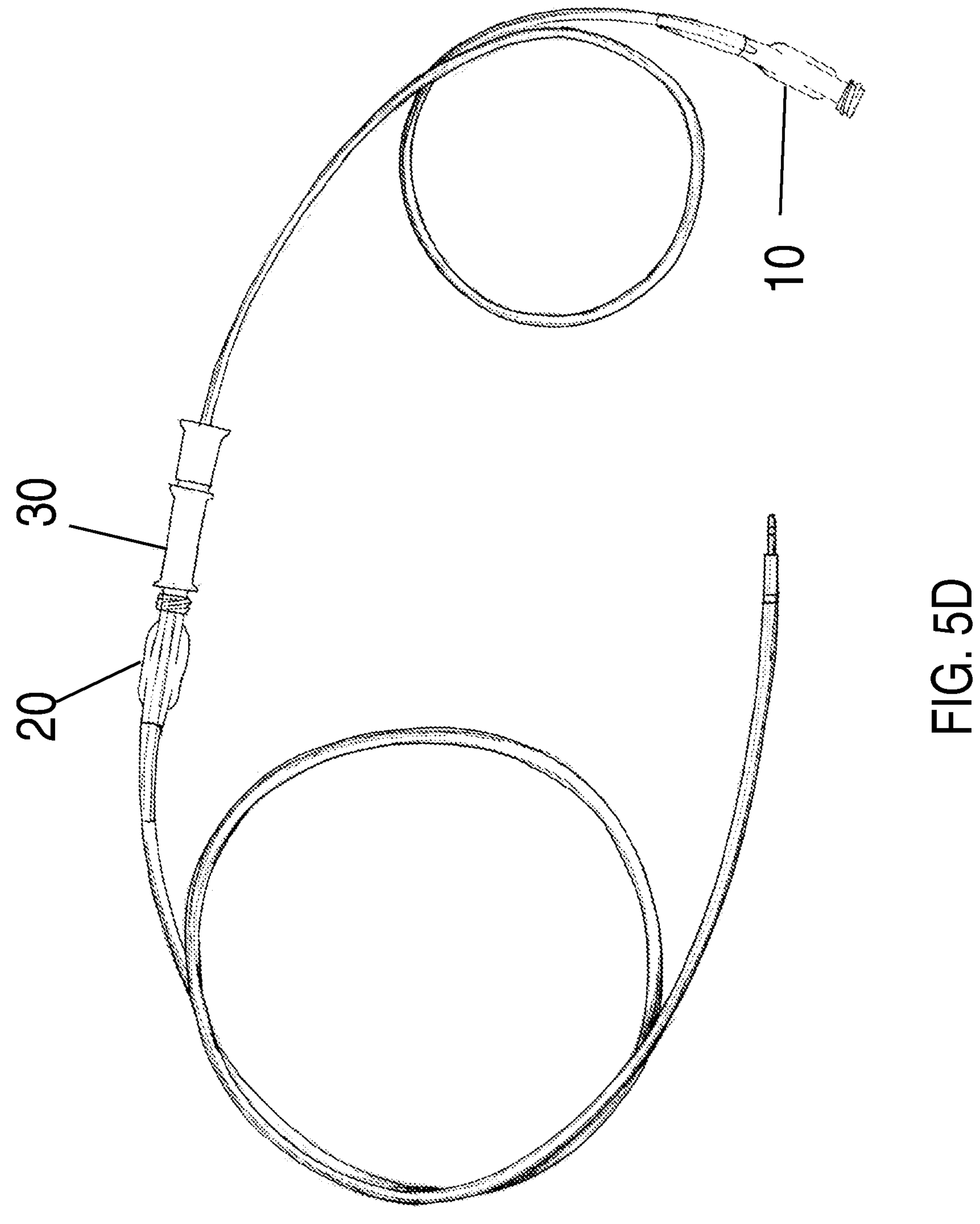
Figure 5E:
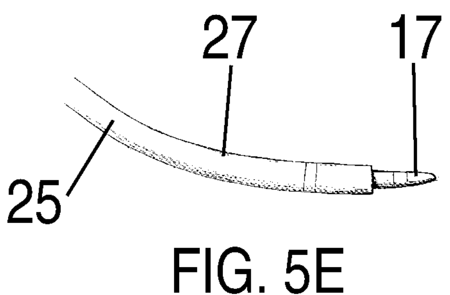
FIG. 5E is a close-up view of the tips of the inner and outer catheters of FIG. 5D.

Guidewires are generally offered in three standard diameters (0.035", 018" and 014") and in lengths ranging from 90 cm to 300 cm. They are further offered with a wide range of different tip configurations that are generally more flexible than the proximal length of the wire, but still optimised with differing mechanical properties as needed to enhance overall pushability and trackability in specific clinical situations. Thus, Interventionalists can select from a broad range of guidewires of differing sizes, lengths, and mechanical properties as needed to optimise their preferred technique for reaching and crossing any vascular lesion. But, even with this wide range of guidewire designs, very few lesions can be reached and crossed without the use of a supporting catheter. In general terms, the Interventionalist will pre-load a relatively long guidewire 2 into a relatively shorter support catheter before introducing the tip of the wire into the vasculature (e.g., vessel 5 as shown in FIG. 4B). The wire is then advanced until the accumulated resistance makes further wire advancement difficult, at which point the tip of support catheter is advanced closer to the tip of the wire, which provides new support for the proximal span of the wire within the vessel, and enables the tip to then be advanced deeper into the vasculature. This sequential advance and support process is repeated as needed until the tip of the wire reaches the lesion. If the lesion to be treated is highly calcified, very long, totally occluded (see FIG. 3) or any combination of these complicating factors, a significant amount of added wire support may needed to push the tip of the guidewire into and through the complex lesion. For these reasons, an Interventionalist attempting to treat complex lesions (or a series of lesions) that are distant from the access site will often employ two support catheters coaxially arranged in a telescoping configuration, as shown in FIG. 4A, so that the level of support provided to the guidewire tip as it is advanced to the lesion can be more effectively optimised and maximised along the way: support for the tip can be increased when more pushability is required by closing the distance between the tips of the telescoping support catheter and advancing them closer to the guidewire tip; or the flexibility can be increased by retracting the outer support catheter tip 27 from the inner support catheter tip 17, and retracting both catheter tips from the guidewire tip (See FIG. 4B). If, once the tip of the guidewire reaches the lesion, a significantly increased level of support is needed to advance the guidewire tip into and through the lesion, then both support catheter tips can be advanced up to the tip of the guidewire (see FIG. 5E) to maximise tip stiffness and pushability. Once the tip of the guidewire has been advanced through the lesion the Interventionalist will often attempt to open a wider channel by advancing the support catheter(s) through the lesion over the wire, and then proceed to use the wire and support catheter(s) to reach and cross additional lesions deeper in the vasculature. Once the wire is in place across the lesion(s) the support catheter(s) are removed, leaving the wire in place and ready for use to introduce and advance the interventional devices (typically an angioplasty balloon and/or athetherectomy device) used to open the lesion as needed to restore adequate blood flow in the vessel.

Conventional telescoping support catheter systems typically include a relatively short and stiff single lumen catheter through which a relatively longer and more flexible single lumen catheter can pass in a telescoping manner (FIG. 4A). Both single lumen catheters 10, 20 are equipped on the proximal (rear) end (closest to the Interventionalist) with a hub 16, 26 that facilitates introduction of a guidewire (or other suitably sized device) and standard tapered luer connection with a syringe to allow injection of saline, radiopaque contrast media or other fluids needed to perform the interventional procedure. The hubs 26 can optionally comprise luer locking outer threads 19, 29 to facilitate a more stable and secure connection to other luer equipped devices, when required. The outer catheter lumen is sized to accommodate sliding passage of the inner catheter, and the inner catheter lumen is sized to accommodate sliding passage of a guidewire with a diameter between 0.038" and 0.010", but preferably of either 0.035", 0.018" or 0.014" in diameter. As shown in FIG. 4A, both catheters are typically equipped with at least one radiopaque marker band 13, 23 at their distal tips 17, 27 to enable fluoroscopic visualisation of the tip while in use (FIG. 3), and one or both catheter shafts may be further equipped with a hydrophilic coating along at least a portion of its distal length. In use, these two catheters are free to independently slide relative to one another to optimise, as needed, the length and relative stiffness of the distal section of the telescoping assembly. Those skilled in the art can appreciate that an Interventionalist often needs to use both hands to achieve and maintain optimal positioning of the telescoping catheters while simultaneously advancing the guidewire deeper into the vasculature system, and that a significant level of dexterity is needed to control three devices with two hands while viewing the system's advance within the artery on a fluoroscopic monitor. Often, the Interventionalist needs to let go of one or more of the devices in order to maximise control of the other devices, which adds time to the procedure while exposing the Interventionalist, clinical staff, and the patient to greater levels of x-ray radiation. In many situations, the Interventionalist needs to simultaneously maximise the support, stability, and control of both catheter tips, especially when trying to select a specific arterial branch (FIG. 4B). Upon reaching the lesion, the Interventionalist often needs to maximise the amount of penetrating force that the guidewire and/or catheter system can bring to bear on the lesion while attempting to cross it, which is especially the case if the lesion is a Chronic Total Occlusion (CTO).

Those skilled in the art know that successfully advancing the guidewire from the vascular access site to and across the lesion is very often the most difficult and time consuming part of the clinical procedure. An Interventionalist attempting to treat a series of distal complex lesions often starts the procedure with a telescoping support catheter system (FIG. 4A) in order to maximise the chances of success within the shortest time possible, thus minimising the amount of radiation exposure on themselves and their staff, as well as minimising the amount of fluoroscopic contrast agent and anticoagulative medications injected into the patient's bloodstream. Successful manipulation of two support catheters and a guidewire over the course of a long procedure requires considerable skill, experience, patience, dexterity and teamwork. The Interventionalist periodically needs assistance to hold and stabilise one of the 3 devices what adjusting or safely advancing the other two devices deeper into the vascular system. Thus, the clinical benefits of a conventional telescoping support catheter system are partially offset by the complexity of keeping them stable relative to one another, and the guidewire, during the clinical procedure.

In these challenging clinical situations, it would be advantageous to be able to temporarily lock the catheters together in an optimal telescoping configuration, thus stabilising them as a single unit and enabling them both to be safely and efficiently operated by the Interventionalist with one hand, while freeing up the other hand free to independently advance and control the guidewire safely and effectively while attempting to reach and cross distal lesions deep in the patient's vascular system. It is contemplated that the telescoping catheter system disclosed herein can be configured to provide one or more of these advantages.

In use, and as further described herein, it is contemplated that the addition of a clutch apparatus positioned over the inner catheter can be used by the Interventionalist to selectively couple and de-couple the telescoping catheters into a fixed position relative to one another. It is contemplated that the disclosed clutch apparatus can allow the Interventionalist to selectively lock and unlock the two catheters together at any point during an interventional procedure, without impinging on the inner catheter lumen through which the guidewire must always slide freely or compromising the mechanical integrity of the inner catheter wall. Thus, it is contemplated that the addition of a clutch apparatus to a telescoping catheter system can allow an Interventionalist to more easily control all three (or more) devices under a wider variety of clinical situations, thereby expanding clinical utility, improving patient and staff safety, and reducing medical procedure time/cost.

Telescoping Catheter System with Clutch Apparatus

Disclosed herein in various aspects, and with reference to FIGS. 5A-11B, is a telescoping catheter system 100 that is equipped with a clutch apparatus 30 as further disclosed herein. As further described herein, it is contemplated that modification of a conventional telescoping catheter design (such as shown in FIG. 4A) to include a clutch apparatus 30 of any of the forms disclosed herein (such as those shown in FIGS. 5A-11B) can enable an Interventionalist to safely and selectively couple or de-couple the inner and outer telescoping catheters 10, 20 during an interventional procedure.

As shown in FIGS. 5A-5D, in various aspects, the clutch apparatus 30 can have a sliding fit over the inner catheter shaft at a location proximal of (behind) the outer catheter hub 26. In these aspects, the telescoping catheter system 100 can comprise an inner catheter 10 having a lumen 12 configured to receive a guidewire 2 (See FIG. 8B) and an outer catheter 20 having a lumen 22 configured to receive the inner catheter. The clutch apparatus 30 can be configured to selectively couple and decouple the inner and outer catheters 10, 20. When the clutch apparatus 30 couples the inner and outer catheters 10, 20 together, the inner and outer catheters can be configured for axial movement as a unitary structure, and when the inner and outer catheters are decoupled, the inner and outer catheters can be configured for independent telescoping axial movement. In exemplary aspects, when the clutch apparatus 30 couples the inner and outer catheters 10, 20 together for axial movement as a unitary structure, the inner and outer catheters are configured to freely rotate relative to one another. Thus, although relative axial movement is restricted, rotational movement of the catheters is not restricted, which can be advantageous in various situations, such as when attempting to steer the system into a vascular side branch, or when encountering and steering past obstructions within the vasculature.

In further aspects, and as further described herein, the inner catheter 10 and the outer catheter 20 can have respective lengths, and the clutch apparatus 30 is configured to couple the inner and outer catheters together via (a) compressive contact at multiple points (e.g., any selected point) along the length of the inner catheter; and (b) connection of the clutch apparatus to the hub 26 of the outer catheter 20. Thus, the various embodiments of the clutch apparatus 30 disclosed herein can couple the inner and outer catheters 10, 20 only when the clutch apparatus is both activated to grip the inner catheter and connected (or permanently fixed) to the hub 26 of the outer catheter 20.

In exemplary aspects, because the clutch apparatus 30 can slide along the length of the inner catheter shaft 15, it is contemplated that the clutch apparatus 30 can be configured to effect selective gripping of the inner catheter shaft at any location along the length of the inner catheter shaft, provided the clutch apparatus is positioned proximal (rearward) of the outer catheter hub 26.

In some exemplary aspects, the engagement between the clutch apparatus 30 (in any of the embodiments disclosed further herein) and the inner catheter 10 does not interfere with free movement of the guidewire 2 within the lumen 12 of the inner catheter. Thus, in any of the embodiments disclosed herein or depicted in FIGS. 6A-11B, it is contemplated that when the disclosed clutch apparatus 30 is actuated to couple the inner catheter 10 to the outer catheter 20, the clutch apparatus is sized and shaped to prevent the possibility of interference with the free movement of the guidewire 2 within the lumen 15 of the inner catheter 10, or to in any way compromise the mechanical integrity of the wall of the inner catheter 10.

Embodiments with a Sliding Collar

In various aspects, and with reference to FIGS. 6A-9C and 11A-11B, the outer catheter 20 can have a proximal, rear end 24 having a hub 26. A portion 14 of the inner catheter can protrude proximally from the outer catheter (See FIG. 5A). In exemplary aspects, the clutch apparatus 30 can comprise a body 32 configured to be fixedly secured to the hub 26 of the outer catheter 20. More particularly, it is contemplated that the body 32 can comprise a front end 34 that has an outer surface that defines a taper 37, which can be complementary to a luer taper 21 formed by an inner surface 28 of hub 26. In use, it is contemplated that the the front end 34 can further comprise a rotatable swivel 36 that is sized and shaped to allow the clutch apparatus to rotate or freely spin when received within the hub 26, thereby providing axial locking of the clutch apparatus 30 to the hub 26 but allowing for relative rotational movement between the clutch apparatus and the hub 26 of the outer catheter 20.

The clutch apparatus 30 can further comprise a collar 50 slidably coupled to and positioned over the body 32. The collar 50 can be configured for axial movement relative to the body 32 in order to selectively engage or disengage the portion 14 of the inner catheter 10 (e.g., the portion of the inner catheter shaft 15) that protrudes proximally from the outer catheter 20 (e.g., from the hub 26 of the outer catheter).

In exemplary aspects, and with reference to FIGS. 6A-6D, the collar 50 can comprise an inner surface 52 that faces the body 32 of the clutch apparatus 30. The body 32 of the clutch apparatus 30 can comprise a wall 38 that defines a lumen 40. The wall 38 of the body 32 of the clutch apparatus 30 can define an opening 42 in communication with the lumen 40.

Figure 6A:
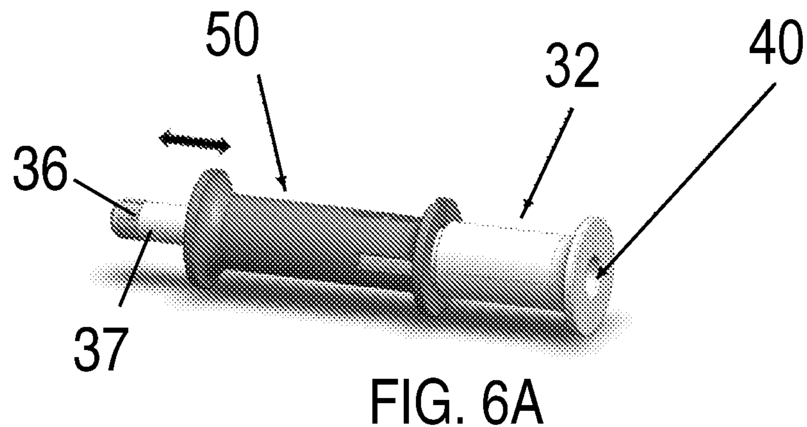
FIGS. 6A-6D depict an exemplary clutch apparatus having a sliding collar.

In some aspects, a projection 54 (optionally, a plurality of projections) can extend radially inwardly from the inner surface 52 of the collar 50. In these aspects, the clutch apparatus 30 can further comprise an insert 60 positioned within the opening 42 of the wall 38 of the body 32 of the clutch apparatus. As shown in FIGS. 6C-6D, the slidable collar 50 can be movable between: a first, rearward position along a length of the body of the clutch apparatus in which the projection is axially spaced from the insert (FIG. 6C); and a second, forward position along the length of the body of the clutch apparatus in which the projection engages the insert to effect radial movement of the insert into the lumen to engage the inner catheter and axially fix the inner catheter with respect to the outer catheter (FIG. 6D). Optionally, to permit such movement, the collar 50 can define an axial slot that receives a fixed projection that projections outwardly from the body 32 as shown in 6A, with the axial slot allowing for axial translation of the collar relative to the fixed projection and the fixed projection serving to limit the amount of permitted translation of the collar.

In some optional aspects, the projection 54 can be radially deformable and define a contact surface 56. In these aspects, when the slidable collar 50 is in the first, rearward position (FIGS. 6B-6C), the contact surface 56 of the projection 54 can engage the wall 38 of the body 32 of the clutch apparatus 30 and have a first radial position. When the slidable collar 50 is in the second, forward position (FIG. 6D), the contact surface 56 of the projection 54 can engage the insert 60 and have a second radial position that is radially inward of the first radial position.

In exemplary aspects, the insert 60 can be rigid or substantially rigid. Exemplary materials for insert 60 include, for example and without limitation, Stainless Steel, Polycarbonate, Polysulfone, Polyvinyl Chloride (PVC), or High Density Polyethylene (HDPE).

As explained above, in some optional aspects, the body 32 of the clutch apparatus 30 can comprise a front end 34 that comprises a rotatable swivel 36 that is configured to provide an interference fit within the hub 26 of the outer catheter 20 while also permitting independent rotational movement of the first and second catheters 10, 20.

Figure 6B:
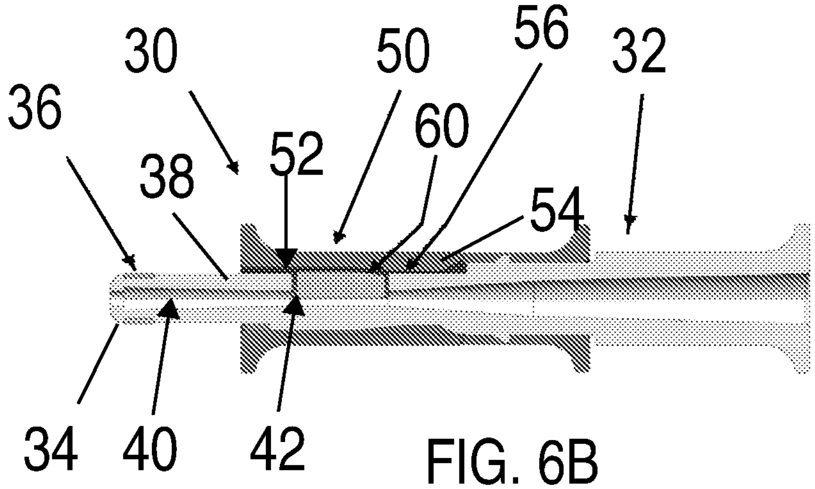
Figure 6C:
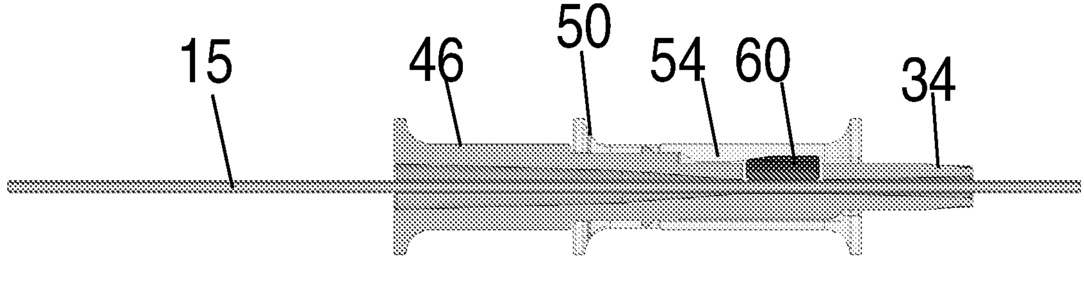
Figure 6D:
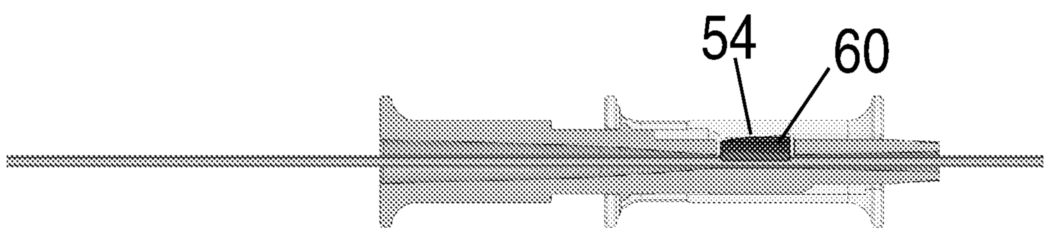

With reference to FIG. 6B, it is seen that the lumen 40 of the body 32 of the clutch apparatus 30 is sized and shaped to accommodate sliding passage on the shaft 15 of the inner catheter 10 when the collar 50 is in a rearward (retracted) position that allows the insert 60 to move freely over the catheter shaft 15 without impinging upon it. In this embodiment, actuation of the clutch apparatus 30 to couple the inner catheter 10 to the outer catheter 20 can be initiated by advancing the collar in a forward direction to cause the internal projection(s) 54 (e.g., ramps) of the collar 50 to forcibly depress and fixate the insert 60 into a position that impinges on the external surface of the shaft 15 of the inner catheter 10. It is contemplated that the insert 60 and the projection(s) 54 can be sized and shaped to ensure that, when the clutch apparatus 30 is actuated, the wall of the inner catheter 10 is securely gripped but not compressed to a degree that causes the lumen 12 of the shaft 15 of the inner catheter to be restricted to the point of interference with free guidewire movement within the lumen 12. The coupling of the inner catheter 10 to the outer catheter 20 can be completed by advancing and securing the clutch apparatus into the hub 26 of the outer catheter 20. As further described above, it is contemplated that the clutch apparatus 30 can further comprise a rotatable swivel 36 that is designed to provide an interference fit within the hub 26 of the outer catheter 20. In use, it is contemplated that the rotating swivel can couple the clutch apparatus 30 to the hub 26 in a manner that prevents telescoping motion between the two catheters, but still allows free rotational motion between the two catheters.

In use, it is contemplated that decoupling of the two telescoping catheters 10, 20 can be accomplished by first disengaging the clutch apparatus 30 from the hub 26 of the outer catheter and then retracting the collar 50 to release the compression of the insert 60 onto/against the shaft 15 of the inner catheter 10.

Figure 7A:
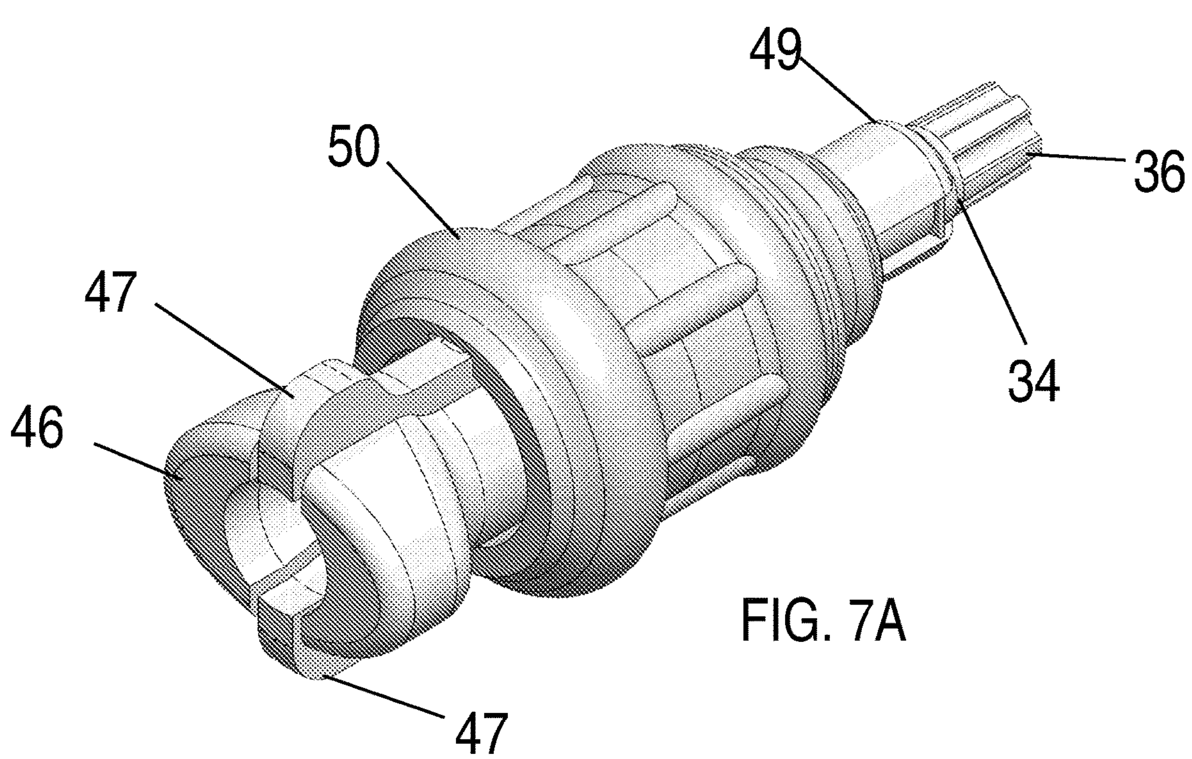
FIGS. 7A-7C depict an exemplary clutch apparatus having a sliding collar.
Figure 7B:
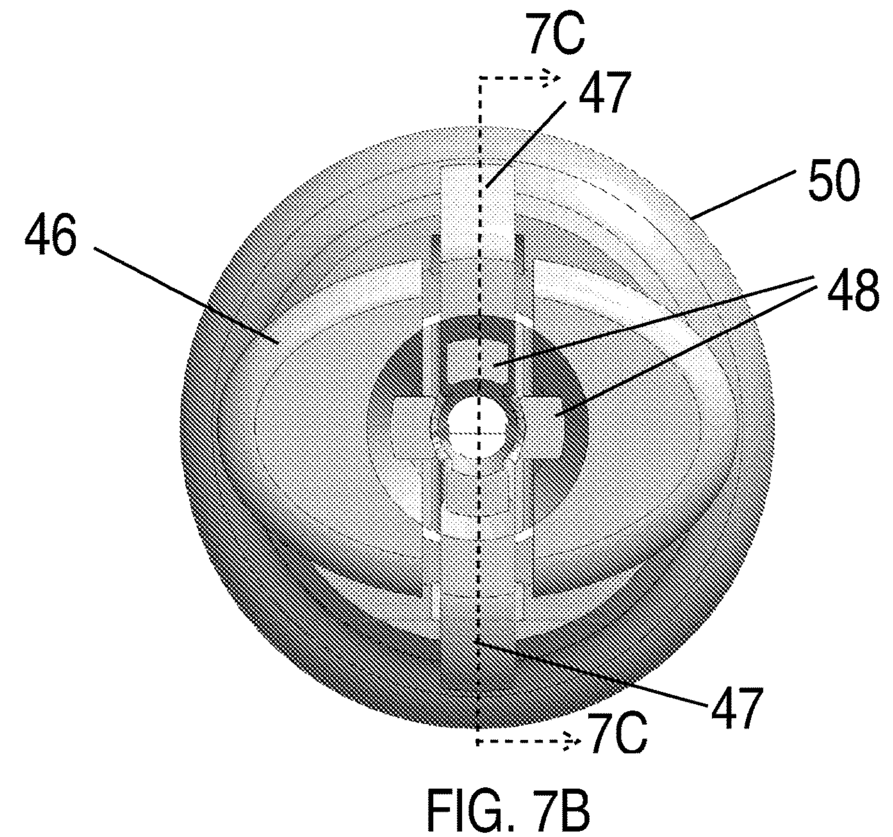
Figure 7C:
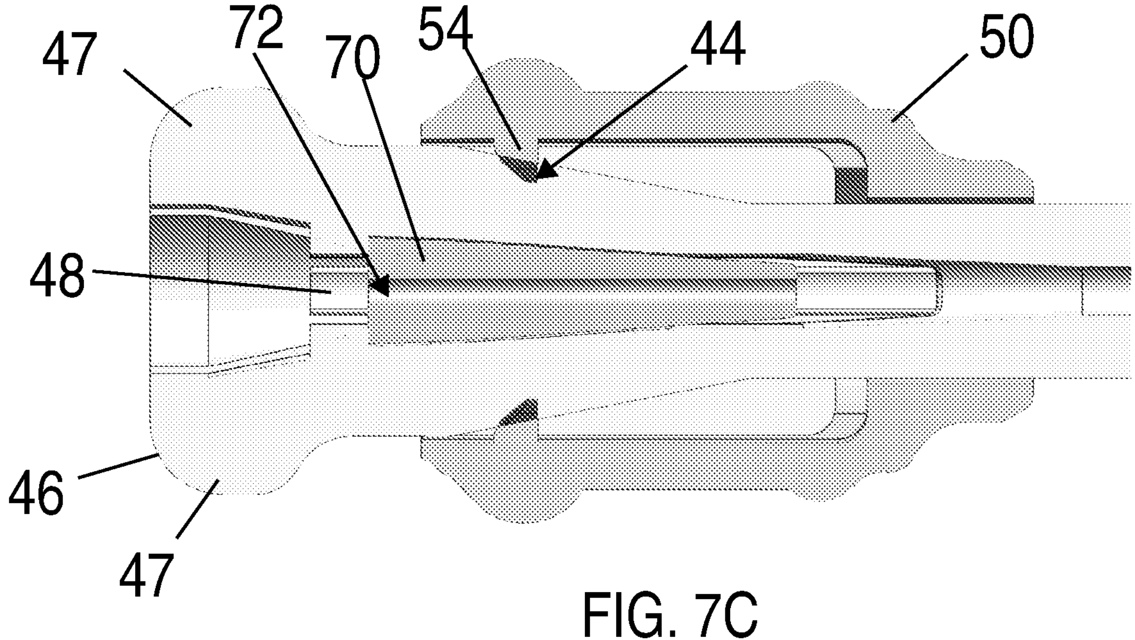

In further exemplary aspects, and with reference to FIGS. 7A-7C, the collar 50 can comprise an inner surface 52 that faces the body of the clutch apparatus, and the body 32 of the clutch apparatus 30 can comprise a wall 38 that defines a lumen 40, with the telescoping catheter system 100 further comprising a compressible insert 70 positioned within the lumen 40. In these aspects, the compressible insert 70 can define a central bore 72 configured to receive a portion of the inner catheter. In exemplary aspects, it is contemplated that the compressible insert 70 can comprise, for example and without limitation, Nylon Elastomer, Silicone, or Low Density Polyethylene (LDPE).

In some aspects, the collar 50 can comprise at least one projection 54 that extends radially inwardly from the inner surface 52 of the collar. In these aspects, the wall 38 of the body 32 of the clutch apparatus 30 can have an outer surface that defines at least one groove 44. It is contemplated that the collar 50 can be slidably movable relative to the body 32 of the clutch apparatus 30 between: a first, forward position in which the at least one projection 54 of the collar 50 is received within the at least one groove 44 of the wall of the body of the clutch apparatus and does not cause radial compression of the compressible insert 70; and a second, rearward position in which the at least one projection of the collar engages the outer surface of the wall of the body of the clutch apparatus to cause radial compression of the compressible insert to grip a portion of the inner catheter 10. In use, when the collar is in the second, rearward position, it is contemplated that the compressible insert 70 can grip and remain engaged with the inner catheter 10 until the collar is moved to the first, forward position.

In further aspects, the body 32 of the clutch apparatus 30 can comprise a rear portion 46 that extends rearwardly from the collar 50, and the rear portion of the body of the clutch apparatus can be selectively radially compressible to grip a portion of the inner catheter 10. Thus, in some optional aspects, the clutch apparatus 30 can be configured to mechanically engage the shaft 15 of the inner catheter 10 in two distinct ways: (1) by movement of the slidable collar 50; or by manual compression (e.g., by hand) of the rear portion 46 of the body 32. For example, the rear portion 46 of the body of the clutch apparatus can be selectively radially compressible from a first (uncompressed) configuration, and upon removal of the force that causes the radial compression (e.g., upon release of the rear portion from the hand of an Interventionalist), the rear portion 46 of the body of the clutch apparatus can return to the first configuration to disengage the inner catheter.

Optionally, in exemplary aspects, the rear portion 46 of the body of the clutch apparatus can comprise at least one tab 47 (optionally, a plurality of tabs) that extends radially outwardly from the wall 38 of the body 32 of the clutch apparatus 30, and the at least one tab can be selectively engagable by a portion of a hand to effect manual gripping of the inner catheter 10. As one example, and as shown in FIG. 7B, the at least one tab 47 can comprise first and second tabs that are on opposite sides of the lumen 40 of the wall 38 of the body 32 of the clutch apparatus 30.

Optionally, in further exemplary aspects, the rear portion 46 of the body 32 of the clutch apparatus 30 can further comprise at least one projection 48 (e.g., a plurality of inner projections) extending radially inwardly from the wall 38 of the body 32 of the clutch apparatus 30. In these aspects, the at least one projection 48 can be configured to grip the inner catheter 10 upon radial compression of the rear portion 46 of the body of the clutch apparatus. Optionally, as shown in FIG. 7C, it is contemplated that the insert 70 can be positioned forwardly (distal) of the projection(s) 48, and the projection(s) can help retain the insert 70 within the lumen 40. In further optional aspects, it is contemplated that the at least one tab 47 can be positioned rearwardly (proximal) of the projection(s) as shown in FIG. 7C.

As explained above, in some optional aspects, the body 32 of the clutch apparatus 30 can comprise a front end 34 that comprises a rotatable swivel 36 that is configured to provide an interference fit within the hub 26 of the outer catheter 20 while also permitting independent rotational movement of the first and second catheters 10, 20.

As explained above, the embodiment disclosed with reference to FIGS. 7A-7D has a sliding collar design that is similar to the embodiment disclosed with reference to FIGS. 6A-6B, but the rigid impcompressible insert 60 has been replaced with a soft, compressible insert 70. In exemplary configurations of the embodiment depicted in FIGS. 7A-7D, the coupling action is accomplished by two exposed tabs 47 that can be actuated by the Interventionalist in either one of two ways: either on an intermittent temporary basis by first manually depressing and releasing the tabs 47 to forcibly collapse and relax the soft compressible insert 70 onto and off of the shaft 15 of the inner catheter 10; or retracting the collar 50 to compress and maintain the tabs 47 (or other portion of the body 32) in the position required to forcibly collapse the soft compressible insert 70 onto the shaft 15 of the inner catheter 10 for an interval of time, freeing up the Interventionalist's hand for other activity, until such time as de-coupling is required. To accomplish such decoupling, the Interventionalist advances the collar 50 back to the decoupled position and releases the grip of the compressible insert 70 on the shaft 15 of the inner catheter 10.

Figure 8A:
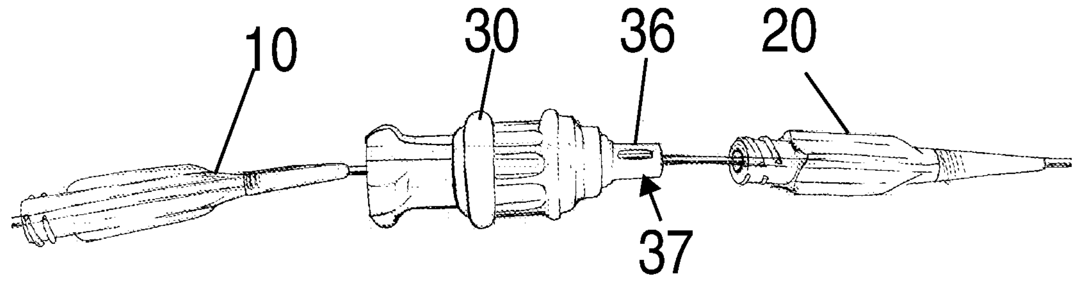
Figure 8E:
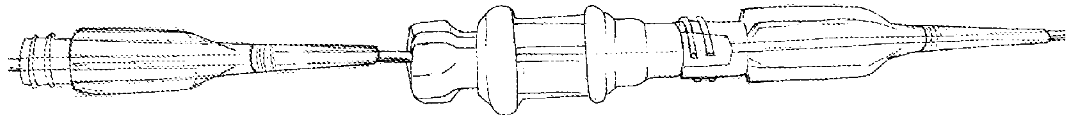

FIGS. 8A-8E show an exemplary sequence of steps that an Interventionalist would follow to operate the clutch apparatus of FIGS. 7A-7D in clinical practice. In FIG. 8A, the collar 50 is in the forward position, and the clutch apparatus 30 is free to slide over the inner catheter 10. As discussed above, the tabs 47 can be manually depressed and released to impart a temporary intermittent coupling of the clutch apparatus 30 to the inner catheter 10, for example, in order to conveniently adjust the relative position of the inner catheter 10 with respect to the outer catheter 20. FIGS. 8B-8C schematically indicate how the collar 50 can be alternately advanced or retracted to hold or release the tabs 47 as desired by the Interventionalist. FIG. 8E shows how the clutch apparatus 30 can be advanced and inserted into the hub 26 of the outer catheter 20 with the tabs 47 fixed in the depressed state (by the collar) in order to couple the inner and outer catheters together, until such time as the Interventionalist desires to restore free telescoping movement of the inner and outer catheters, by either advancing the collar 50 or, alternatively, disconnecting the clutch apparatus 30 from the hub 26 of the outer catheter 20.

Figure 9A:
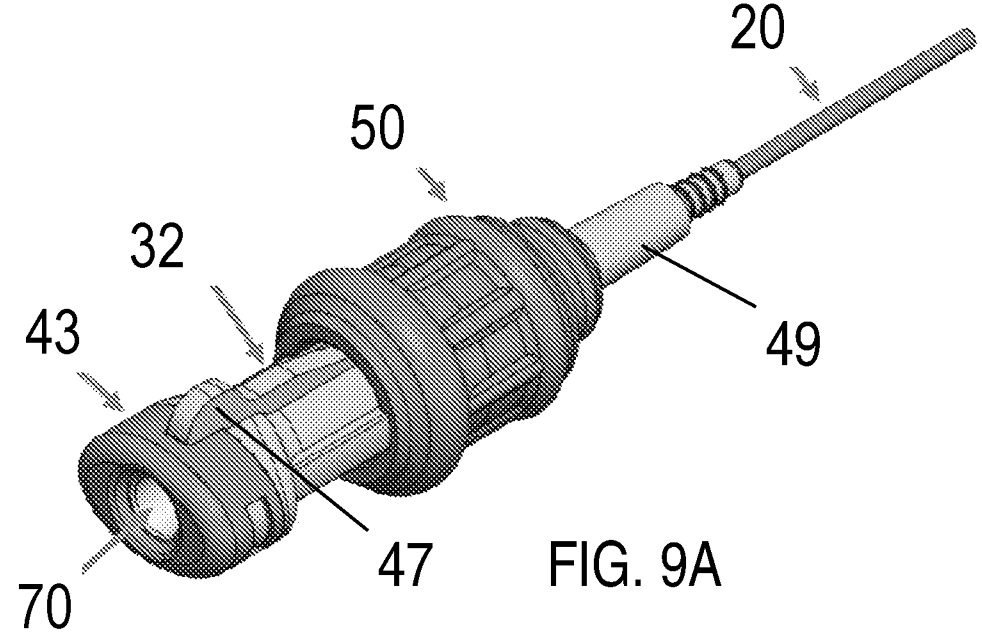
FIGS. 9A-9C depict another exemplary clutch apparatus that is permanently secured to the outer catheter hub.
Figure 9B:
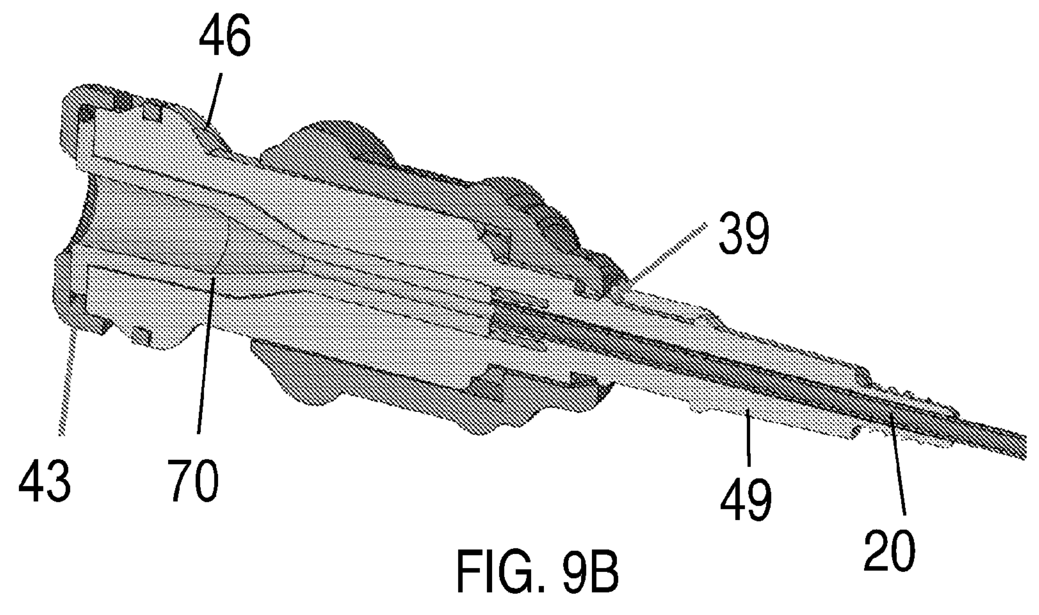
Figure 9C:
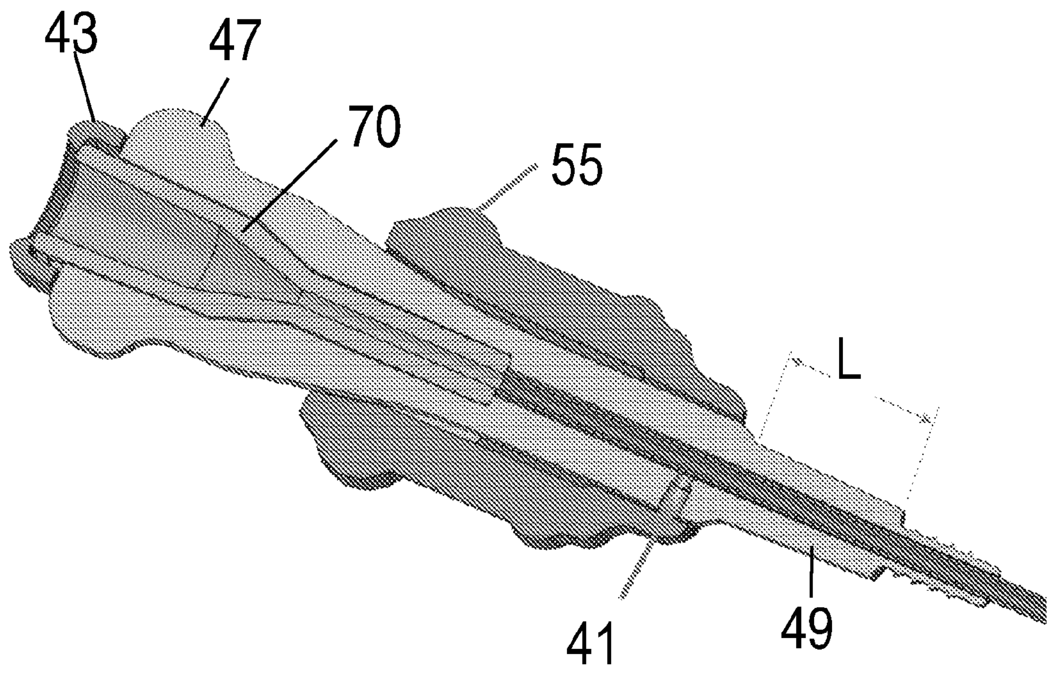

In various aspects, and with reference to FIGS. 9A-9C, it is contemplated that the body of the clutch apparatus 30 can be permanently secured to or integrally formed with the hub 26 of the outer catheter 20. In exemplary aspects, the clutch apparatus 30 of FIGS. 9A-9C can employ the same gripping mechanisms as the clutch apparatus disclosed with respect to FIGS. 8A-8E. Briefly, the clutch apparatus 30 of FIGS. 9A-9C can have a body 32 and a slidable collar 50, and the slidable collar can be retracted to a position in which engagement between the collar and the body 32 causes compression of an insert 70. Optionally, as shown in FIG. 9B, at least one radial projection 39 (e.g., a bump) can extend outwardly from the wall 38 of the body 32 and be configured to engage a portion of the slidable collar 50 to retain the collar in an activated/engaged position. As shown in FIG. 9B, a glue hole 41 can be provided through which an adhesive can a be injected during manufacturing to bond the outer catheter 20 to the body 32 of the clutch apparatus 30. In further aspects, as shown in FIGS. 9A-9C, the clutch apparatus 30 can comprise a proximal cap 43 that secures the compressible insert 70 in position within the body 32 of the clutch apparatus, preventing the insert from being pulled out by sliding frictional contact with the inner catheter 10 during an interventional procedure.

Single-Piece Clutch Apparatus

Figure 10A:
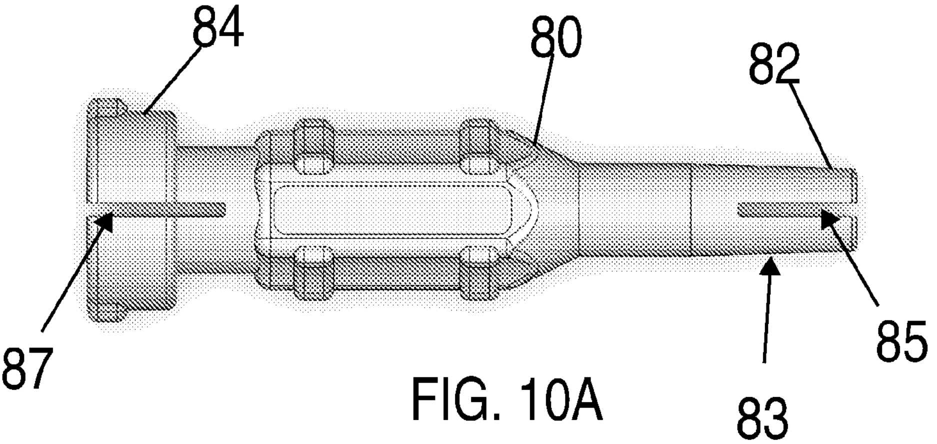
FIG. 10A depicts a side elevation view of an exemplary single-piece clutch apparatus having two axially spaced gripping portions as disclosed herein.
Figure 10B:
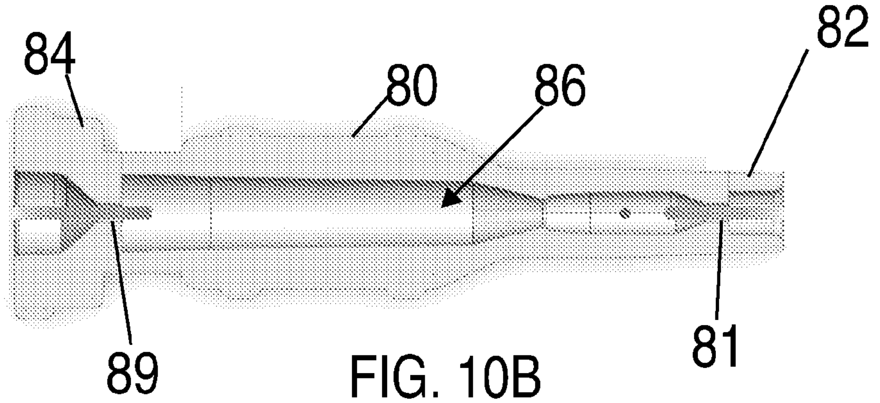
FIG. 10B is an internal section view of the clutch apparatus of FIG. 10A.
Figure 10C:
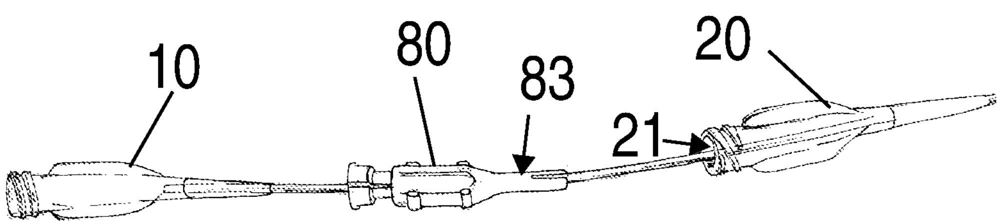
FIG. 10C is a schematic illustration of the clutch apparatus of FIG. 10A in position on telescoping catheters.
Figure 10D:
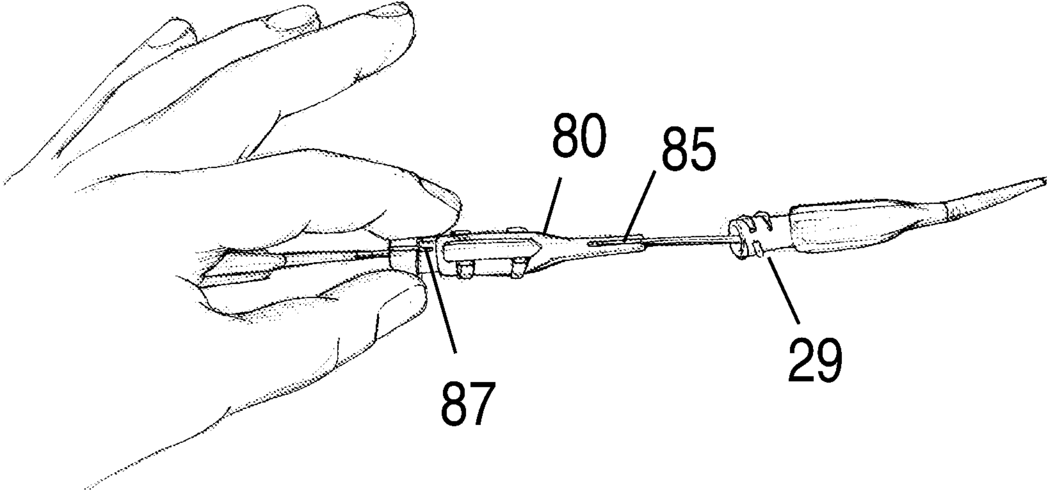
FIG. 10D is a schematic illustration of manual compression of a first, proximal gripping portion of the clutch apparatus to grip an inner catheter shaft.
Figure 10E:
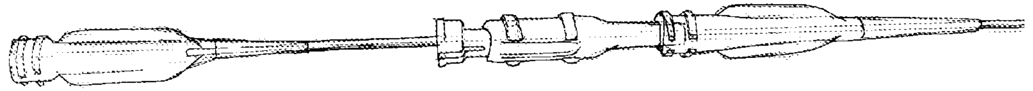
FIG. 10E is a schematic illustration of a second, distal gripping portion of the clutch apparatus being inserted into an outer catheter hub to compress the distal gripping portion and lock the inner catheter shaft.

In exemplary aspects, and with reference to FIGS. 10A-10G, the clutch apparatus 30 can comprise a unitary body 80 having opposing front and rear end portions 82, 84 and defining a lumen 86 extending between the front and rear end portions. In these aspects, each of the front and rear end portions 82, 84 of the unitary body 80 can be radially compressible. The front end portion 82 of the unitary body 80 can be configured for receipt within the hub 26 of the outer catheter 20, and upon receipt of the front end portion of the unitary body within the hub of the outer catheter, inner surfaces 28 of the hub of the outer catheter can be configured to effect radial compression of the front end portion of the unitary body to grip the inner catheter 10. In exemplary aspects, it is contemplated that the inner surfaces 28 of the hub 26 of the outer catheter 20 can define a luer taper (as is conventionally found in Luer lock connections), and the front end portion 82 of the unitary body 80 can define a complementary taper 83 and at least one slot 85 that permits radial compression of the front end portion as the front end portion is advanced within the hub 26 of the outer catheter 20. In further aspects, the rear end portion 84 of the unitary body 80 can be selectively radially compressible by a radially inward force to permit manual gripping of the inner catheter. Optionally, the rear end portion 84 of the unitary body 80 can define at least one slot 87 that promotes selective radial compression. As shown in FIG. 10B, the unitary body 80 can further comprise at least one first gripping projection 81 extending radially inwardly from an inner surface of the front end portion 82 and at least one second gripping projection 89 extending radially inwardly from an inner surface of the rear end portion 84. In use, the projection(s) 81 can be configured to engage the inner catheter 10 when the front end portion 82 is received within the hub 26 of the outer catheter 20, and the projection(s) 89 can be configured to engage the inner catheter 10 when the rear end portion 84 is manually radially compressed.

Figure 10F:
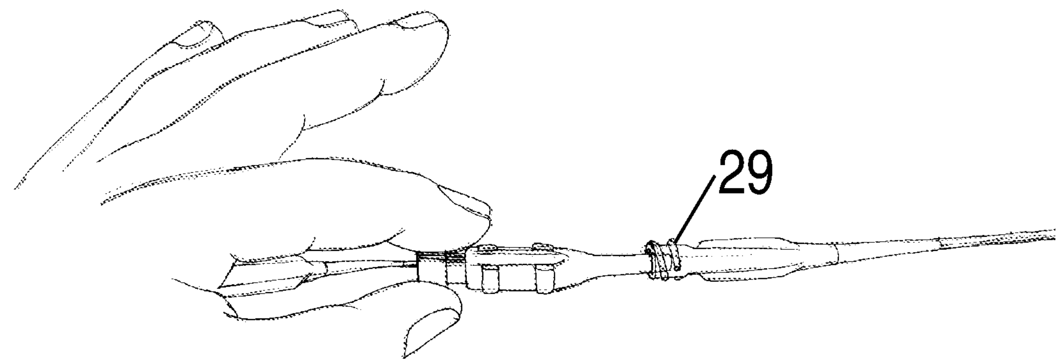
FIG. 10F is a schematic illustration of both the first and second gripping portions being activated at the same time to grip the inner catheter shaft in two axially spaced locations.
Figure 10G:
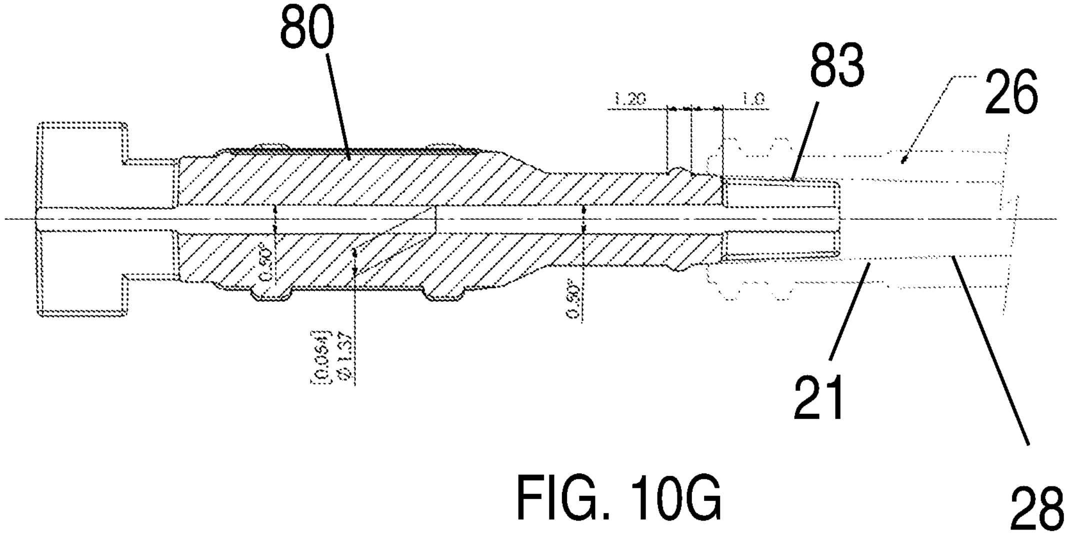
FIG. 10G is a sectional view of the clutch apparatus of FIG. 10A, showing the distal (forward) end of the clutch apparatus received within the hub of an outer catheter.

Thus, it is contemplated that the clutch apparatus depicted in FIGS. 10A-10G can provide similar functionality to the embodiments shown in FIGS. 7A-9C without the need for an insert or collar. In this embodiment, the unitary body 80 includes two gripping mechanisms, a first manual gripping mechanism (the rear end portion 84) dedicated to providing an intermittent grip on the inner catheter shaft 15 that can be manually established and maintained by the Interventionalist; and a second gripping mechanism (the front end portion 82) that is actuated by insertion of the front end portion into the hub 26 of the outer catheter 20, which exerts a compressive grip onto the inner catheter shaft and restricts telescoping movement between the inner and outer catheters 10, 20. Still further, it is contemplated that the compressive coupling grip of the clutch apparatus 30 onto the inner catheter shaft 15 can be significantly increased by simultaneous actuation of both mechanisms, as shown in FIG. 10F, without increasing the possibility of restricting guidewire movement within the lumen of the inner catheter, or compromising the mechanical integrity of the inner catheter wall. It is still further contemplated that the simultaneous activation of both gripping mechanisms can effectively double the gripping force, minimizing the possibility of one of the catheter tips sliding when contacting an obstruction within the vasculature.

Clutch Apparatus with Connector

Figure 11A:
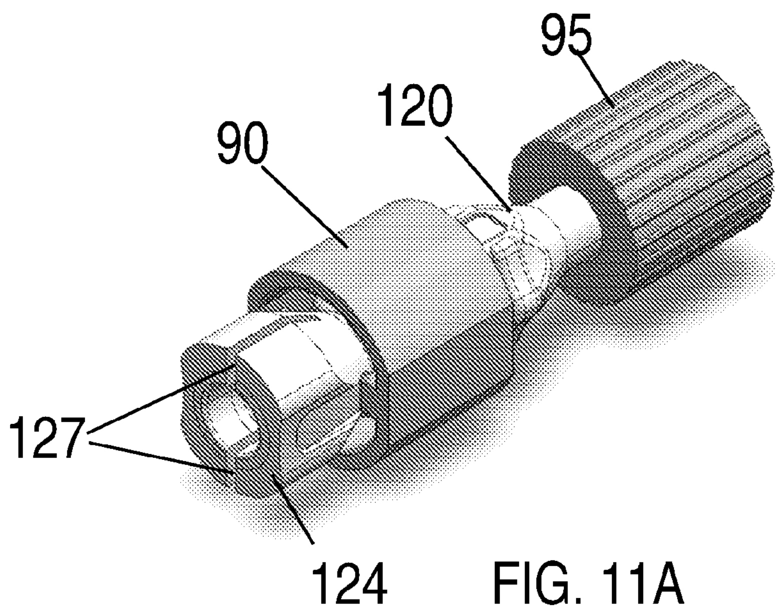
FIG. 11A is a perspective view of a clutch apparatus having a sliding locking collar and a threaded connector collar as disclosed herein.
Figure 11B:
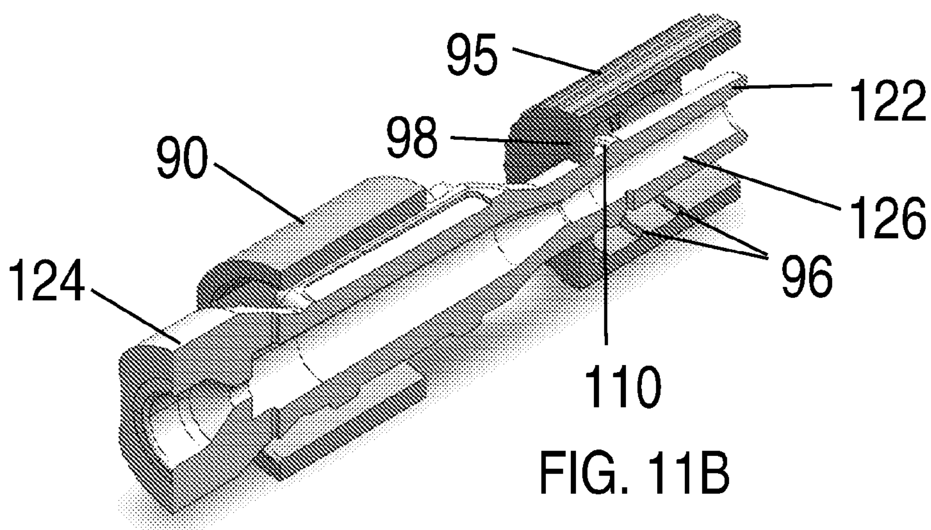
FIG. 11B is a sectional view of the clutch apparatus of FIG. 11A.

In further exemplary aspects, and with reference to FIGS. 11A-11B, the clutch apparatus 30 can comprise a body 120 having opposing front and rear end portions 122, 124 and defining a lumen 126 extending between the front and rear end portions. The rear end portion 124 of the body can be radially compressible, and the front end portion 122 of the body can configured for receipt within a hub 26 of the outer catheter 20. Optionally, in order to promote compression of the rear end portion 124, at least one slot 127 (optionally, a plurality of slots) can be provided within the rear end portion. The clutch apparatus 30 can further comprise a locking collar 90 that surrounds a portion of the body 120 and is selectively slidable between: a first, forward position along a length of the body of the clutch apparatus 30 in which the locking collar is axially spaced from the rear end portion 124 of the body; and a second, rearward position along the length of the body in which the locking collar surrounds at least a portion of the rear end portion 124 of the body to effect radial compression of the rear end portion of the body. In exemplary aspects, and as shown in FIG. 11A, the locking collar 90 can comprise at least one radial projection that extends radially inwardly from the inner surface of the locking collar and is configured to engage and radially compress the rear end portion 124 when the locking collar is in the second, rearward position.

In further exemplary aspects, the hub 26 of the outer catheter 20 comprises external threads 29, and the clutch apparatus 30 further comprises a connector collar 95 that surrounds at least a portion of the front end portion 122 of the body 120 and comprises internal threads 96 that engage the external threads 29 of the hub 26 of the outer catheter 20. In these aspects, it is contemplated that the connector collar 95 can be threaded onto the threads of the hub 26 to provide controlled axial movement of the inner catheter relative to the outer catheter while the clutch is being coupled to the outer catheter 20. Optionally, the outer surface of the front end portion 122 of the body 120 can define an outwardly projecting shoulder surface 110 that is engaged by a corresponding shoulder 98 of the connector collar that is positioned rearwardly (proximally) of the shoulder surface 110. In these aspects, as the connector collar 95 is axially advanced, the shoulder 98 engages the shoulder surface 110 so that axial movement of the connector collar effects corresponding axial movement of the body 120 into the hub 26. It is further contemplated that the shoulder surface 110 can have an outer diameter that is greater than the inner diameter of the shoulder 98 of the connector collar 95, thereby retaining the connector collar in place. In use, it is contemplated that the connector collar 95 can provide a forward drive function without clutching or gripping the inner catheter.

In use, it is contemplated that the proximal, retractable locking collar 90 can allow an Interventionalist to optionally maintain compressive fixation to the shaft 15 of the inner catheter 10 without needing to manually compress and hold down the rear end portion of the body. Additionally, when the rotating connector collar 95 is rotated to secure the clutch apparatus 30 to the outer catheter 20, the connection travel serves to drive the inner catheter 10 forward within the outer catheter over a discrete distance defined by the engagement length of the internal threads 96 of the connector collar 95 and the external threads 29 of the hub 26 of the outer catheter 20.

Additional Comments on Disclosed Embodiments

As further explained herein, the disclosed clutch apparatus 30 can be configured to grip or engage the shaft 15 of the inner catheter 10 without impinging upon the lumen 12 of the inner catheter, thereby avoiding damage to the inner catheter and avoiding interference with axial translation of the guidewire 2. As one example, the inner catheter can have an outer diameter and the body of the clutch apparatus 30 can have an inner diameter that is only slightly larger than the outer diameter of the inner catheter (providing a minimal clearance), with the compressive force applied to the clutch apparatus to grip the inner catheter resulting in a compressive deformation that is only slightly greater than the minimal clearance provided between inner catheter and clutch apparatus prior to compression. In exemplary aspects, it is contemplated that the permitted compressive deformation can vary depending on the specific catheters and guidewires that are used. However, in some non-limiting examples, the compressive deformation can range from about 0.001 inches to about 0.05 inches.

As further explained herein, the disclosed embodiments of the clutch apparatus 30 can permit an Interventionalist to mechanically set, maintain, and release clutching/gripping action at any point along the exposed portions of the inner catheter shaft. As further explained herein, at least the disclosed embodiments of the clutch apparatus described with reference to FIGS. 6A-9C and 11A-11B can permit an Interventionalist to selectively spin the inner catheter shaft relative to the outer catheter shaft while the inner catheter shaft is being mechanically gripped/locked (e.g., using a sliding collar).

As further explained herein, at least the disclosed embodiments of the clutch apparatus described with reference to FIGS. 7A-11B can permit an Interventionalist to manually clutch/grip and release any point along the exposed portions of the inner catheter shaft. As further explained herein, at least the disclosed embodiments of the clutch apparatus described with reference to FIGS. 10A-11B can permit an Interventionalist to selectively spin the inner catheter shaft relative to the outer catheter shaft while the inner catheter shaft is being manually gripped/locked.

As further explained herein, at least the embodiments of the clutch apparatus described with reference to FIGS. 6A-6D can permit an Interventionalist to selectively spin the inner catheter shaft relative to the outer catheter shaft when both (a) the inner shaft is gripped/locked by the clutch apparatus and (b) the clutch apparatus is connected to the hub of the outer catheter.

As further explained herein, at least the embodiments of the clutch apparatus described with reference to FIGS. 10A-10G can permit an Interventionalist to simultaneously grip the inner catheter shaft at two locations, effectively doubling the locking force. As further explained herein, these embodiments can also provide a proximal gripping/clutch mechanism that enables the Interventionalist to hold and advance the inner catheter into an optimal position relative to the outer catheter, as well as a distal gripping/clutch mechanism that can lock the inner catheter into the determined optimal position by insertion into the outer catheter hub.

As further explained herein, at least the embodiments of the clutch apparatus described with reference to FIGS. 11A-11B can permit an Interventionalist to provide a controlled, incremental advancement of the inner catheter tip after the inner catheter shaft has been gripped by the clutch apparatus.

Exemplary and Alternative Embodiments

Various exemplary and alternative embodiments of the disclosed telescoping catheter system and clutch apparatus are contemplated.

For example, it is contemplated that the system can include more than two catheters of differing lengths coaxially arranged in a telescoping fashion.

Although some dimensional ranges have been provided herein, it is contemplated that any appropriate inner and outer catheter dimensions (length, ID and OD, cross sectional geometry, and the like) can be used without departing from the scope of the disclosed embodiments.

Although the catheters depicted in the drawings are single lumen catheters, it is contemplated that the system can include catheters have multiple lumens and/or varying lumen geometries.

It is contemplated that any conventional catheter materials and constructions (polymeric, metallic, composites, braid reinforced, solid monolithic, and the like) can be used without departing from the purpose of the disclosed system.

It is contemplated that any desired catheter tip geometries and characteristics (e.g., radiopacity, taper, hardness, sharpness, and the like) can be used within the disclosed systems.

It is contemplated that any desired catheter surface modifications (e.g., hydrophilic coating type, coating length, and the like) can be used within the disclosed systems.

Although various embodiments disclosed herein describe particular locations for gripping or providing fixed engagement with the inner catheter, it is contemplated that any gripping or engagement location can be used.

Although various actuators for the disclosed clutch apparatuses have been described herein, it is contemplated that additional or alternative actuators (e.g., thumb depressor, thumb wheel, lever, and/or the like) for the clutch apparatuses can be provided.

Although various clutch mechanisms for securing the inner catheter have been disclosed, it is contemplated that other approaches are possible. For example, it is contemplated that the clutch apparatus can use compression or stretching of a surrounding elastomeric tube, an inflatable bladder, a spring plate, or any other variable means involving the storage and release of a compressive force.

Although the disclosed clutch apparatuses and catheter systems are generally described with reference to vascular procedures, it is contemplated that the disclosed apparatuses and catheter systems can likewise be employed in non-vascular interventional or diagnostic procedures, such as, for example and without limitation, endoscopic procedures in the gastrointestinal system or laparoscopic procedures within the peritoneal cavity.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A telescoping catheter system comprising: an inner catheter having a lumen configured to receive a guidewire; an outer catheter having a lumen configured to receive the inner catheter; and a clutch apparatus configured to selectively couple and decouple the inner and outer catheters, wherein when the clutch apparatus couples the inner and outer catheters together, the inner and outer catheters are configured for axial movement as a unitary structure, and wherein when the inner and outer catheters are decoupled, the inner and outer catheters are configured for independent telescoping axial movement.

Aspect 2: The telescoping catheter system of aspect 1, wherein when the clutch apparatus couples the inner and outer catheters together for axial movement as a unitary structure, the inner and outer catheters are configured to freely rotate relative to one another.

Aspect 3: The telescoping catheter system of aspect 1 or aspect 2, wherein the inner catheter and the outer catheter have respective lengths, and wherein the clutch apparatus is configured to couple the inner and outer catheters together via (a) compressive contact at multiple points along the length of the inner catheter and (b) connection of the clutch apparatus to a hub of the outer catheter.

Aspect 4: The telescoping catheter system of any one of the preceding aspects, wherein the outer catheter has a proximal, rear end having a hub, wherein a portion of the inner catheter protrudes proximally from the outer catheter, and wherein the clutch apparatus comprises: a body fixedly secured to the hub of the outer catheter; and a collar slidably coupled to and positioned over the body, wherein the collar is configured for axial movement relative to the body in order to selectively engage or disengage the portion of the inner catheter that protrudes proximally from the outer catheter.

Aspect 5: The telescoping catheter system of aspect 4, wherein the collar comprises an inner surface that faces the body of the clutch apparatus, wherein the body of the clutch apparatus comprises a wall that defines a lumen, the wall of the body of the clutch apparatus defining an opening in communication with the lumen, the telescoping catheter system further comprising: a projection extending radially inwardly from the inner surface of the collar; and an insert positioned within the opening of the wall of the body of the clutch apparatus, wherein the slidable collar is movable between: a first, rearward position along a length of the body of the clutch apparatus in which the projection is axially spaced from the insert; and a second, forward position along the length of the body of the clutch apparatus in which the projection engages the insert to effect radial movement of the insert into the lumen to engage the inner catheter and axially fix the inner catheter with respect to the outer catheter.

Aspect 6: The telescoping catheter system of aspect 5, wherein the projection is radially deformable and defines a contact surface, wherein when the slidable collar is in the first, rearward position, the contact surface of the projection engages the wall of the body of the clutch apparatus and has a first radial position, and wherein when the slidable collar is in the second, forward position, the contact surface of the projection engages the insert and has a second radial position that is radially inward of the first radial position.

Aspect 7: The telescoping catheter system of any one of aspects 4-6, wherein the body of the clutch apparatus comprises a front end that comprises a rotatable swivel that is configured to provide an interference fit within the hub of the outer catheter while also permitting independent rotational movement of the first and second catheters.

Aspect 8: The telescoping catheter system of any one of aspects 5-7, further comprising a guidewire extending through the lumen of the inner catheter, wherein the engagement between the insert and the inner catheter does not interfere with free movement of the guidewire within the lumen of the inner catheter.

Aspect 9: The telescoping catheter system of any one of aspects 5-8, wherein the insert is rigid.

Aspect 10: The telescoping catheter system of aspect 4, wherein the collar comprises an inner surface that faces the body of the clutch apparatus, wherein the body of the clutch apparatus comprises a wall that defines a lumen, the telescoping catheter system further comprising a compressible insert positioned within the lumen defined by the wall of the body of the clutch apparatus, the compressible insert defining a central bore configured to receive a portion of the inner catheter.

Aspect 11: The telescoping catheter system of aspect 10, wherein the collar comprises at least one projection that extends radially inwardly from the inner surface of the collar, wherein the wall of the body of the clutch apparatus has an outer surface that defines at least one groove, wherein the collar is slidably movable relative to the body of the clutch apparatus between: a first, forward position in which the at least one projection of the collar is received within the at least one groove of the wall of the body of the clutch apparatus and does not cause radial compression of the compressible insert; and a second, rearward position in which the at least one projection of the collar engages the outer surface of the wall of the body of the clutch apparatus to cause radial compression of the compressible insert to grip a portion of the inner catheter.

Aspect 12: The telescoping catheter system of aspect 11, wherein when the collar is in the second, rearward position, the compressible insert grips and remains engaged with the inner catheter until the collar is moved to the first, forward position.

Aspect 13: The telescoping catheter system of any one of aspects 10-12, wherein the body of the clutch apparatus comprises a rear portion that extends rearwardly from the collar, wherein the rear portion of the body of the clutch apparatus is selectively radially compressible to grip a portion of the inner catheter.

Aspect 14: The telescoping catheter system of aspect 13, wherein the rear portion of the body of the clutch apparatus is selectively radially compressible from a first configuration, and wherein upon removal of a force that causes radial compression of the rear portion of the body of the clutch apparatus, the rear portion of the body of the clutch apparatus is configured to return to the first configuration to disengage the inner catheter.

Aspect 15: The telescoping catheter system of aspect 14, wherein the rear portion of the body of the clutch apparatus comprises at least one tab that extends radially outwardly from the wall of the body of the clutch apparatus, and wherein the at least one tab is selectively engagable by a portion of a hand to effect manual gripping of the inner catheter.

Aspect 16: The telescoping catheter system of aspect 15, wherein the at least one tab comprises first and second tabs that are on opposite sides of the lumen of the wall of the body of the clutch apparatus.

Aspect 17: The telescoping catheter system of aspect 15 or aspect 16, wherein the rear portion of the body of the clutch apparatus further comprises at least one projection extending radially inwardly from the wall of the body of the clutch apparatus, and wherein the at least one projection is configured to grip the inner catheter upon radial compression of the rear portion of the body of the clutch apparatus.

Aspect 18: The telescoping catheter system of any one of aspects 10-17, wherein the body of the clutch apparatus comprises a front portion that extends forwardly of the collar, wherein the front portion of the body of the clutch apparatus comprises a rotatable swivel that is configured to provide an interference fit within the hub of the outer catheter while also permitting independent rotational movement of the first and second catheters.

Aspect 19: The telescoping catheter system of any one of aspects 10-17, wherein the body of the clutch apparatus is permanently secured to or integrally formed with a hub of the outer catheter.

Aspect 20: The telescoping catheter system of any one of aspects 1-3, wherein the clutch apparatus comprises: a unitary body having opposing front and rear end portions and defining a lumen extending between the front and rear end portions, each of the front and rear end portions of the unitary body being radially compressible, wherein the front end portion of the unitary body is configured for receipt within a hub of the outer catheter, and wherein upon receipt of the front end portion of the unitary body within the hub of the outer catheter, inner surfaces of the hub of the outer catheter are configured to effect radial compression of the front end portion of the unitary body to grip the inner catheter, and wherein the rear end portion of the unitary body is selectively radially compressible by a radially inward force to permit manual gripping of the inner catheter.

Aspect 21: The telescoping catheter system of any one of aspects 1-3, wherein the clutch apparatus comprises: a body having opposing front and rear end portions and defining a lumen extending between the front and rear end portions, wherein the rear end portion of the body is radially compressible, and wherein the front end portion of the unitary body is configured for receipt within a hub of the outer catheter; and a locking collar that surrounds a portion of the body and is selectively slidable between: a first, forward position along a length of the unitary body of the clutch apparatus in which the locking collar is axially spaced from the rear end portion of the unitary body; and a second, rearward position along the length of the unitary body in which the locking collar surrounds at least a portion of the rear end portion of the unitary body to effect radial compression of the rear end portion of the unitary body.

Aspect 22: The telescoping catheter system of aspect 21, wherein the hub of the outer catheter comprises external threads, the telescoping catheter system further comprising a connector collar that surrounds at least a portion of the front end portion of the body and comprises internal threads that engage the external threads of the hub of the outer catheter.

Aspect 23: The telescoping catheter system of aspect 22, wherein the connector collar is configured to apply radial inward force to the front end portion of the body to grip the inner catheter, and wherein rotation of the connector collar is configured to provide controlled axial movement of the inner catheter relative to the outer catheter.

Aspect 24: A method comprising: using the clutch apparatus of the telescoping catheter system of any one of aspects 1-23 to couple the inner and outer catheters together; and with the inner and outer catheters coupled together, selectively advancing a guidewire through the inner catheter.

Aspect 25: The method of aspect 24, further comprising: using the clutch apparatus to decouple the inner and outer catheters.

Aspect 26: The method of any one of aspects 24-25, further comprising axially translating the inner catheter relative to the outer catheter.

Aspect 27: A clutch apparatus for selectively coupling and decoupling inner and outer catheters, wherein a portion of the inner catheter protrudes proximally from the outer catheter, the clutch apparatus comprising: a body configured to be secured to a hub of the outer catheter; and a collar slidably coupled to and positioned over the body, wherein the collar is configured for axial movement relative to the body in order to selectively engage or disengage the portion of the inner catheter that protrudes proximally from the outer catheter, wherein the clutch apparatus is configured to couple the inner and outer catheters together such that the inner and outer catheters are capable of axial movement as a unitary structure.

Aspect 28: A clutch apparatus as recited in any one of aspects 1-23.

Although the foregoing invention has been described in some detail by way of illustration and example for purposes of clarity of understanding, certain changes and modifications may be practiced within the scope of the appended claims.

What is claimed is:

1. A telescoping catheter system comprising:

an inner catheter having a lumen configured to receive a guidewire;

an outer catheter having a lumen configured to receive the inner catheter, wherein the outer catheter has a proximal, rear end having a hub, wherein a portion of the inner catheter protrudes proximally from the outer catheter; and a clutch apparatus configured to selectively couple and decouple the inner and outer catheters, wherein the clutch apparatus comprises:

a body fixedly secured to the hub of the outer catheter; and a collar slidably coupled to and positioned over the body, wherein the collar is configured for axial movement relative to the body in order to selectively engage or disengage the portion of the inner catheter that protrudes proximally from the outer catheter, wherein the collar comprises an inner surface that faces the body of the clutch apparatus, wherein the body of the clutch apparatus comprises a wall that defines a lumen, the wall of the body of the clutch apparatus defining an opening in communication with the lumen:

a projection extending radially inwardly from the inner surface of the collar; and an insert positioned within the opening of the wall of the body of the clutch apparatus, wherein the slidable collar is movable between:

a first, rearward position along a length of the body of the clutch apparatus in which the projection is axially spaced from the insert; and a second, forward position along the length of the body of the clutch apparatus in which the projection engages the insert to effect radial movement of the insert into the lumen to engage the inner catheter and axially fix the inner catheter with respect to the outer catheter, wherein when the clutch apparatus couples the inner and outer catheters together, the inner and outer catheters are configured for axial movement as a unitary structure, and wherein when the inner and outer catheters are decoupled, the inner and outer catheters are configured for independent telescoping axial movement.

2. The telescoping catheter system of claim 1, wherein the projection is radially deformable and defines a contact surface, wherein when the slidable collar is in the first, rearward position, the contact surface of the projection engages the wall of the body of the clutch apparatus and has a first radial position, and wherein when the slidable collar is in the second, forward position, the contact surface of the projection engages the insert and has a second radial position that is radially inward of the first radial position.

3. The telescoping catheter system of claim 1, wherein the body of the clutch apparatus comprises a front end that comprises a rotatable swivel that is configured to provide an interference fit within the hub of the outer catheter while also permitting independent rotational movement of the first and second catheters.

4. The telescoping catheter system of claim 1, further comprising a guidewire extending through the lumen of the inner catheter, wherein the engagement between the insert and the inner catheter does not interfere with free movement of the guidewire within the lumen of the inner catheter.

5. The telescoping catheter system of claim 1, wherein the insert is rigid.

6. A telescoping catheter system comprising:

an inner catheter having a lumen configured to receive a guidewire;

an outer catheter having a lumen configured to receive the inner catheter, wherein the outer catheter has a proximal, rear end having a hub, wherein a portion of the inner catheter protrudes proximally from the outer catheter; and a clutch apparatus configured to selectively couple and decouple the inner and outer catheters, wherein the clutch apparatus comprises:

a body fixedly secured to the hub of the outer catheter; and a collar slidably coupled to and positioned over the body, wherein the collar is configured for axial movement relative to the body in order to selectively engage or disengage the portion of the inner catheter that protrudes proximally from the outer catheter, wherein when the clutch apparatus couples the inner and outer catheters together, the inner and outer catheters are configured for axial movement as a unitary structure, and wherein when the inner and outer catheters are decoupled, the inner and outer catheters are configured for independent telescoping axial movement, wherein the collar comprises an inner surface that faces the body of the clutch apparatus, wherein the body of the clutch apparatus comprises a wall that defines a lumen, the telescoping catheter system further comprising a compressible insert positioned within the lumen defined by the wall of the body of the clutch apparatus, the compressible insert defining a central bore configured to receive a portion of the inner catheter, and wherein the collar comprises at least one projection that extends radially inwardly from the inner surface of the collar, wherein the wall of the body of the clutch apparatus has an outer surface that defines at least one groove, wherein the collar is slidably movable relative to the body of the clutch apparatus between:

a first, forward position in which the at least one projection of the collar is received within the at least one groove of the wall of the body of the clutch apparatus and does not cause radial compression of the compressible insert; and a second, rearward position in which the at least one projection of the collar engages the outer surface of the wall of the body of the clutch apparatus to cause radial compression of the compressible insert to grip a portion of the inner catheter.

7. The telescoping catheter system of claim 6, wherein the body of the clutch apparatus comprises a front end that comprises a rotatable swivel that is configured to provide an interference fit within the hub of the outer catheter while also permitting independent rotational movement of the first and second catheters.

8. The telescoping catheter system of claim 6, wherein when the collar is in the second, rearward position, the compressible insert grips and remains engaged with the inner catheter until the collar is moved to the first, forward position.

9. The telescoping catheter system of claim 6, wherein the body of the clutch apparatus comprises a rear portion that extends rearwardly from the collar, wherein the rear portion of the body of the clutch apparatus is selectively radially compressible to grip a portion of the inner catheter.

10. The telescoping catheter system of claim 9, wherein the rear portion of the body of the clutch apparatus is selectively radially compressible from a first configuration, and wherein upon removal of a force that causes radial compression of the rear portion of the body of the clutch apparatus, the rear portion of the body of the clutch apparatus is configured to return to the first configuration to disengage the inner catheter.

11. The telescoping catheter system of claim 10, wherein the rear portion of the body of the clutch apparatus comprises at least one tab that extends radially outwardly from the wall of the body of the clutch apparatus, and wherein the at least one tab is selectively engagable by a portion of a hand to effect manual gripping of the inner catheter.

12. The telescoping catheter system of claim 11, wherein the at least one tab comprises first and second tabs that are on opposite sides of the lumen of the wall of the body of the clutch apparatus.

13. The telescoping catheter system of claim 11, wherein the rear portion of the body of the clutch apparatus further comprises at least one projection extending radially inwardly from the wall of the body of the clutch apparatus, and wherein the at least one projection is configured to grip the inner catheter upon radial compression of the rear portion of the body of the clutch apparatus.

14. The telescoping catheter system of claim 6, wherein the body of the clutch apparatus is permanently secured to or integrally formed with a hub of the outer catheter.

* * * * *